US007582726B2

(12) United States Patent
Chen et al.

(10) Patent No.: US 7,582,726 B2
(45) Date of Patent: Sep. 1, 2009

(54) VEGF RECEPTOR ANTAGONISTS

(75) Inventors: Wen Yuan Chen, Simpsonville, SC (US); Jang P. Park, Greenville, SC (US)

(73) Assignee: GHC Research Development Corporation, Greenville, SC (US)

( * ) Notice: Subject to any disclaimer, the term of this patent is extended or adjusted under 35 U.S.C. 154(b) by 68 days.

(21) Appl. No.: 10/985,013

(22) Filed: Nov. 10, 2004

(65) Prior Publication Data

US 2005/0196396 A1 Sep. 8, 2005

Related U.S. Application Data

(60) Provisional application No. 60/518,295, filed on Nov. 10, 2003.

(51) Int. Cl.
*A61K 38/16* (2006.01)
*A61K 38/17* (2006.01)
*C07K 14/47* (2006.01)

(52) U.S. Cl. ............... 530/324; 530/350; 424/185.1

(58) Field of Classification Search .................. None
See application file for complete search history.

(56) References Cited

U.S. PATENT DOCUMENTS

| 6,204,011 B1 * | 3/2001 | Kendall et al. ............. 435/69.1 |
| 6,359,115 B1 | 3/2002 | Kendall et al. |
| 2003/0092604 A1 | 5/2003 | Davis-Smyth et al. |

FOREIGN PATENT DOCUMENTS

| EP | 1 238 986 A2 | 9/2002 |
| WO | WO 00/37502 | 6/2000 |

OTHER PUBLICATIONS

Ngo et al., 1994, The Protein Folding Problem and Tertiary Structure Prediction, pp. 491-495.*
Attwood et al., The babel of bioinformatics, Oct. 2000, Science 290 (5491): 471-473.*
Skolnick et al, From genes to protein structure and function: novel applications of computational approaches in the genomic era, Jan. 2000, Trends in Biotech. 18(1): 34-39.*
Zhu et al, Investigational New Drugs 17: 195-212, 1999.*
Gasparini et al, The Lancet Oncology 2: 733-740, Dec. 2001.*
Stryer et al, in Biochemistry, Third edition, W H Freeman Company, New York, pp. 31-33, 1998.*
Tao et al, abstract 6.27, FESEB J 15(4): A9, 2001.*
Gennaro et al in Remington's Pharmaceutical Sciences, eighteenth edition, 1990, pp. 1300-1329.*
Fuh et al, J Biol Chemistry 273(18): 11197-11204, 1998.*
Tao et al, J Biol Chem 276(24): 21916-21923, 2001.*
Barleon et al, J Biol Chem 272(16): 10382-10388, 1997.*
Hsieh et al, The Prostate 41: 31-38, 1999.*
Taheri et al, J Biol Chem 278(17): 14632-14639, 2003.*
Leppanen et al, Biochemistry 39: 2370, 2000.*
Altschul et al., "Basic Local Alignment Search Tool", *Journal of Molecular Biology*, 215: pp. 403-410 (1990).
Altschul et al., "Gapped Blast and PSI-Blast: a new generation of protein database search programs", *Nucleic Acids Research*, 25: pp. 3389-3402 (1997).
Cataldo et al., "Inhibition of oncogene STAT3 phosphorylation by a prolactin antagonist, hPRL-G129R, in T47D human breast cancer cells", *International Journal of Oncology*, 17: pp. 1179-1185 (2000).
DeVries, et al., "Thefms-Like Tyrosine Kinase, a receptor for Vascular Endothelial Growth Factor", *Science*, 225: pp. 989-991 (1992).
Dvorak, HF, "Vascular Permeability Factor/Vascular Endothelial Growth Factor: A Critical Cytokine in Tumor Angiogenesis and a Potential Target for Diagnosis and Therapy", *Journal of Clinical Oncology*, 20: pp. 4368-4380 (2002).
Ferrara et al., "Pituitary Follicular Cells Secrete A Novel Heparin-Binding Growth Factor Specific For Vascular Endothelial Cells", *Biochemical and Biophysical Research Communications*, 161: pp. 851-858 (1989).
Ferrara et al., "The Biology of Vascular Endothelial Growth Factor", *Endocrine Reviews*, 18: pp. 4-25 (1997).
Ferrara et al., "The biology of VEGF and its receptors,", *Nature Medicine*, 9: pp. 669-676 (2003).
Gish et. al., "Identification of protein coding regions by database similarity search", *Nature Genetics*, 3: pp. 266-272 (1993).
Gluzman, SV40-Transformed Simian Cells Support the Replication of Early SV40 Mutants, *Cell*, 23: pp. 175-182 (1981).
Hess et al., "Cooperation of Glycolytic Enzymes", *Journal of Advanced Enzyme Regulation*, 7: pp. 149-167 (1968).
Hitzeman et al., "Isolation and Characterization of the Yeast 3-Phosphoglycerokinase Gene (PGK) by an Immunological Screening Technique", *Journal of Biological Chemistry*, 255: pp. 12073-12080 (1980).
Holland et al., "Isolation and identification of Yeast Messenger Ribonucleic Acids Coding for Enolase, Glyceraldehyde-3-phosphate Dehydrogenase and Phosphoglycerate Kinase", *Biochemistry*, 17: pp. 4900-4907 (1978).
Houck et al., "Dual Regulation of Vascular Endothelial Growth Factor Bioavailability by Genetic and Proteolytic Mechanisms", *Journal of Biological Chemistry*, 267: pp. 26031-26037 (1992).
Houck et al., "The Vascular Endothelial Growth Factor Family: Identification of a Fourth Molecular Species and Characterization of Alternative Splicing of RNA", *Molecular Endocrinology*, 5: pp. 1806-1814 (1991).
Jones, "Proteinase Mutants of Saccharomyces Cerevisiae", *Genetics*, 85: pp. 23-33 (1977).
Kim et al., "Potent VEGF blockade causes regression of coopted vessels in a model of neuroblastoma", *Proceedings of the National Academy of Science*, U.S.A., 99: pp. 11399-11404 (2002).
Kingsman et al., "Replication in Saccharomyces Cerevisiae of Plasmid pBR313 Carrying DNA from the Yeast *trp1* Region", *Gene*, 7: pp. 141-152 (1979).
Klagsbrun et al., "Vascular Endothelial Growth Factor and its Receptors", *Cytokine and Growth Factor Reviews*, 7: pp. 259-270 (1996).

(Continued)

*Primary Examiner*—Phuong Huynh
(74) *Attorney, Agent, or Firm*—Foley & Lardner LLP

(57) ABSTRACT

The present invention describes an approach to cancer therapy utilizing novel VEGF receptor antagonists. Specifically, the invention provides peptides and polynucleotides encoding VEGF receptor antagonists and methods of use thereof.

5 Claims, 9 Drawing Sheets

OTHER PUBLICATIONS

Larrivee, et al., "Signaling pathways induced by vascular endothelial growth factor (Review)", *International Journal of Molecular Medicine*, 5: pp. 447-456 (2000).

Lee et al., "Vascular endothelial growth factor-related protein: A ligand and specific activator of the tyrosine kinase receptor Flt4", *Proceedings of the National Academy of Science*, U.S.A., 93: pp. 1988-1992 (1996).

Logan et al., "Adenovirus tripartite leader sequence enhances translation of mRNAs late after infection", *Proceedings of the National Academy of Science*, U.S.A., 81: pp. 3655-3659 (1984).

Madden et al., "Applications of Network Blast Server", *Methods in Enzymology*, 266: pp. 131-141 (1996).

Myoken et al., "Vascular endothelial cell growth factor (VEGF) produced by A-431 human epidermoid carcinoma cells and identification of VEGF membrane binding sites", *Proceedings of the National Academy of Science*, U S A.., 88: pp. 5819-5823 (1991).

Remington's Pharmaceutical Sciences, chapters 27 and 28, pp. 484-528 (Mack Publishing Company 1990).

Siebenlist et al., "*E. coli* RNA Polymerase Interacts Homologously with Two Different Promoters", *Cell*, 20, pp. 269-281 (1980).

Stinchcomb et al., "Isolation and characterization of a yeast chromosomal replicator", *Nature* 282: pp. 39-43 (1979).

Tao et al., "Kinase Insert Domain receptor (KDR) Extracellular Immunoglobulin-like domains 4-7 contain Structural Freatures That Block Receptor Dimerization and Vascular Endothelial Growth Factor-induced Signaling", *Journal of Biological Chemistry*, 276: pp. 21916-21923 (2001).

Terman et al., "Biological properties of VEGF/VPF receptors", *Cancer and Metastasis Reviews*, 15: pp. 159-163 (1996).

Terman, et al., "Identification of a new endothelial cell growth factor receptor tyrosine kinase", *Oncogene*, 6: pp. 1677-1683 (1991).

Tschumper et al., "Sequence of a yeast DNA fragment containing a chromosomal replicator and the TRP1 gene", *Gene*, 10: pp. 157-166 (1980).

Zhang et al., "PowerBlast: A New Network Blast Application for Interactive or Automated Sequence Analysis and Annotation", *Genome Research*, 7: pp. 649-656 (1997).

Matthews, William et al., A Receptor Tyrosine Kinase cDNA Isolated From a Population of Enriched Primitive Hematopoietic Cells and Exhibiting Close Genetic Linkage to c-*kit, Proc. Natl. Acad. Sci. USA*, vol. 88, pp. 9026-9030 (1991).

Wulff et al., "Prevention of Thecal Angiogenesis, Antral Follicular Growth, and Ovulation in the Primate by Treatment with Vascular Endothelial Growth Factor Trap R1R2", Endocrinology, 143(7): pp. 2797-2807 (2008).

Zhang et al., "A Novel Design of Targeted Endocrine and Cytokine Therapy for Breast Cancer", Clinical Cancer Research, 8: pp. 1196-1205 (2002).

Barleon et al., "Mapping of the Sites for Ligand Binding and Receptor Dimerization at the Extracellular Domain of the Vascular Endothelial Growth Factor Receptor FLT-1" The Journal of Biological Chemistry, 272(16): pp. 10382-10388 (1997).

Aiello et al., "Suppression of retinal neovascularization in vivo by inhibition of vascular endothelial growth factor (VEGF) using soluble VEGF-receptor chimeric proteins" Proc. Natl. Acad. Sci. USA, 92: pp. 10457-10461 (1995).

Kendall et al., "Inhibition of vascular endothelial cell growth factor activity by an endogenously encoded soluble receptor" Proc. Natl. Acad. Sci. USA, 90: pp. 10705-10709 (1993).

Holash et al., "VEGF-Trap: A VEGF blocker with potent antitumor effects" PNAS, www.pnas.org, 99(17): pp. 11393-11398 (2002).

MacGabhann, F., et al., "Dimerization of VEGF Receptors and Implications for Signal Transduction: A Computational Study," *Biophysical Chemistry*, vol. 128, 2007, pp. 125-139.

Sato, Y., et al., "Signal Transduction and Transcriptional Regulation of Angiogenesis," *Angiogenesis: From the Molecular to Integrative Pharmacology*, Maragoudakis (ed), Kluwer Academic Publishers, New York, 2000, pp. 109-115.

\* cited by examiner

FPLC Purification (Fractions 11-14, 18, 23)

Staining Gel

Western Blotting

→ 44Kd
→ 22Kd
→ 11Kd

Only fraction 12 contains monomers (barely detectable in Western). The majority Ig4 protein (11kd) formed 44 kd protein presumably a tetramer Figure 8A
SEQ ID NO. 1

KDR Ig 4-7 cDNA atggcattcatcactgtgaaacatcgaaaacagcaggtgcttgaaaccgtagctggcaagcggtcttaccggctctctat
gaaagtgaaggcatttccctcgccggaagttgtatggttaaaagatgggttacctgcgactgagaaatctgctcgctatt
tgactcgtggctactcgttaattatcaaggacgtaactgaagaggatgcagggaattatacaatcttgctgagcataaaa
cagtcaaatgtgtttaaaaaccctcactgccactctaattgtcaatgtgaaaccccagatttacgaaaaggccgtgtcatc
gtttccagacccggctctctacccactgggcagcagacaaatcctgacttgtaccgcatatggtatccctcaacctacaa
tcaagtggttctggcaccccctgtaaccataatcattccgaagcaaggtgtgacttttgttccaataatgaagagtccttt
atcctggatgctgacagcaacatgggaaacagaattgagagcatcactcagcgcatggcaataatagaaggaaagaataa
gatggctagcaccttggttgtggctgactctagaatttctggaatctacatttgcatagcttccaataaagttgggactg
tgggaagaaacataagcttttatatcacagatgtgccaaatgggtttcatgttaacttggaaaaaaatgccgacggaagga
gaggacctgaaactgtcttgcacagttaacaagttcttatacagagacgttacttggattttactgcggacagttaataa
cagaacaatgcactacagtattagcaagcaaaaaatggccatcactaaggagcactccatcactcttaatcttaccatca
tgaatgtttccctgcaagattcaggcacctatgcctgcagagccaggaatgtatacacaggggaagaaatcctccagaag
aaagaaattacaatcagagatcaggaagcaccatacctcctgcgaaacctcagtgatcacacagtggccatcagcagttc
caccactttagactgtcatgctaatggtgtccccgagcctcagatcacttggttttaaaaacaaccacaaaatacaacaag
agcctggaattattttaggaccaggaagcagcacgctgtttattgaaagagtcacagaagaggatgaaggtgtctatcac
tgcaaagccaccaaccagaagggctctgtggaaagttcagcatacctcactgttcaaggaacctcggacaagtctaatta
g Figure 8B.
SEQ ID NO. 2

HMFVAFGSGMESLVEATVGERVRIPAKYLGYPPPEIKWYKNGIPLESNHTIKAGHVLTI
MEVSERDTGNYTVILTNPISK
EKQSHVVSLVVYVPPQIGEKSLISPVDSYQYGTTQTLTCTVYAIPPPHHIHWYWQLEEE
CANEPSQAVSVTNPYPCEEWR
SVEDFQGGNKIEVNKNQFALIEGKNKTVSTLVIQAANVSALYKCEAVNKVGRGERVISF
HVTRGPEITLQPDMQPTEQES
VSLWCTADRSTFENLTWYKLGPQPLPIHVGELPTPVCKNLDTLWKLNATMFSNSTNDIL
IMELKNASLQDQGDYVCLAQD
RKTKKRHCVVRQLTVLERVAPTITGNLENQTTSIGESIEVSCTASGNPPPQIMWFKDNE
TLVEDSGIVLKDGNRNLTIRR
VRKEDEGLYTCQACSVLGCAKVEAFFIIEGAQEK

Figure 9A
SEQ ID NO. 3
Flk-1 B Frag atgcatgtactgacgattatggaagtgagtgaaagagacacaggaaattacactgtcat
cctt
accaatcccatttcaaaggagaagcagagccatgtggtctctctggttgtgtatgtccc
accccagattggtgagaaatc
tctaatctctcctgtggattcctaccagtacggcaccactcaaacgctgacatgtacgg
tctatgccattcctccccgc
atcacatccactggtattggcagttggaggaagagtgcgccaacgagcccagccaagct
gtctcagtgacaaacccatac
ccttgtgaagaatggagaagtgtggaggacttcagggaggaaataaaattgaagttaa
taaaaatcaatttgctctaat
tgaaggaaaaaacaaaactgtaagtaccttgttatccaagcggcaaatgtgtcagctt
tgtacaaatgtgaagcggtca
acaaagtcgggagaggagagagggtgatctccttccacgtgaccagggggtcctgaaatt
actttgcaacctgacatgcag
cccactgagcaggagagcgtgtctttgtggtgcactgcagacagatctacgtttgagaa
cctcacatggtacaagcttgg
cccacagcctctgccaatccatgtgggagagttgcccacacctgtttgcaagaacttgg
atactctttggaaattgaatg
ccaccatgttctctaatagcacaaatgacattttgatcatggagcttaagaatgcatcc
ttgcaggaccaaggagactat
gtctgccttgctcaagacaggaagaccaagaaaagacattgcgtggtcaggcagctcac
agtcctagagcgtgtggcacc
cacgatcacaggaaacctggagaatcagacgacaagtattggggaaagcatcgaagtct
catgcacggcatctgggaatc
cccctccacagatcatgtggttttaaagataatgagacccttgtagaagactcaggcatt
gtattgaaggatgggaaccgg
aacctcactatccgcagagtgaggaaggaggacgaaggcctctacacctgccaggcatg
cagtgttcttggctgtgcaaa
agtggaggcattttttcataatagaaggtgcccaggaaaagtaa

Figure 9B
SEQ ID NO. 4
MHVLTIMEVSERDTGNYTVILTNPISKEKQSHVVSLVVYVPPQIGEKSLISPVDSYQYG
TTQTLTCTVYAIPPPHHIHW
YWQLEEECANEPSQAVSVTNPYPCEEWRSVEDFQGGNKIEVNKQFALIEGKNKTVSTL
VIQAANVSALYKCEAVNKVGR
GERVISFHVTRGPEITLQPDMQPTEQESVSLWCTADRSTFENLTWYKLGPQPLPIHVGE
LPTPVCKNLDTLWKLNATMFS
NSTNDILIMELKNASLQDQGDYVCLAQDRKTKKRHCVVRQLTVLERVAPTITGNLENQT
TSIGESIEVSCTASGNPPPQI
MWFKDNETLVEDSGIVLKDGNRNLTIRRVRKEDEGLYTCQACSVLGCAKVEAFFIIEGA
QEK

VEGF RECEPTOR ANTAGONISTS

CROSS-REFERENCE TO RELATED PATENT APPLICATIONS

This application claims priority to U.S. provisional application 60/518,295, filed on Nov. 10, 2003, which is incorporated herein by reference in its entirety.

BACKGROUND OF THE INVENTION

1. Field of the Invention

The present invention relates to cancer therapy, angiogenesis inhibitors, and methods of use thereof. In particular, the present invention describes vascular endothelial growth factor (VEGF) receptor antagonists and their ability to inhibit angiogenesis.

2. Background of the Invention

Vascular endothelial growth factor (VEGF) is a well characterized pro-angiogenic factor (Larrivee, et al., *Intl. J. Mol. Med.*, 5: 447-456 (2000)). VEGF was purified initially from conditioned media of folliculostellate cells and from a variety of tumor cell lines (Ferrara and Henzel, *Biochem. Biophys. Res. Comm.*, 161:851-858 (1989); Myoken et al., *Proc Natl Acad Sci USA.*, 88:5819-23(1991)). VEGF is a member of the cysteine-knot family of growth factors, which also includes PDGF (Platelet Derived Growth Factor). Recently, a number of VEGF structural homologs have been identified: VEGF-B, VEGF-C, VEGF-D and Placenta Growth Factor (PlGF) (Klagsbrun and D'Amore, Cytokine Growth Factor Rev., 7:259-70 (1996); reviewed in Ferrara et al., *Endocr. Rev.* 18:4-25 (1997).

The human gene encoding VEGF is organized into eight exons, separated by seven introns. Alternative splicing of mRNAs for the VEGF gene results in the generation of five different molecular species, having 121, 145, 165, 189, or 206 amino acid residues in the mature monomer (Tisher et al., 1991; Houck et al., *Mol Endocrinol.*, 5:1806-14 (1991). Only $VEGF_{165}$, which lacks the residues encoded by exon 6, is the mature and active form of VEGF. It binds to heparin and cell surface heparan sulfate proteoglycans, and can be expressed as a free or a cell membrane bound form (Houck et al., *J Biol. Chem.*, 267:26031-7 (1992).

The endothelial proliferative activity of VEGF is known to be mediated by two high affinity tyrosine kinase receptors, flt-1 (VEGFR1) and KDR (VEGFR2), which exist only on the surface of vascular endothelial cells (DeVries, et al., *Science*, 225:989-991 (1992) and Terman, et al., *Oncogene* 6:1677-1683 (1991)). Both the flt-1 and KDR tyrosine kinase receptors have seven immunoglobulin-like (Ig1-7) domains which form the extracellular ligand-binding regions of the receptors, a transmembrane domain which serves to anchor the receptor on the surface of cells in which it is expressed and an intracellular catalytic tyrosine kinase domain which is interrupted by a "kinase insert." While the KDR receptor binds only the VEGF protein with high affinity, the flt-1 receptor also binds placenta growth factor. An additional member of the receptor tyrosine kinases having seven Ig-like domains in the extracellular ligand-binding region is flt-4, which is not a receptor for either VEGF or PlGF, but instead binds to a different ligand: VH1.4.5. The VH1.4.5 ligand has been reported in the literature as VEGF-related protein (VRP) or VEGF-C (Lee et al., *PNAS U.S.A.*, 93:1988-92 (1996); Ferrara et al., (1997)).

The molecular mechanism by which VEGF initiates signaling is thought to be through receptor dimerization followed by receptor autophosphorylation (see, Ferrara et al., *Nat. Med.* 9:669-676 (2003)). In other words, VEGF exerts its biological effects on responsive cells following receptor binding and receptor dimerization. The dimerization of VEGF receptors causes receptor autophosphorylation, which in turn activates MAP kinase (MAPK) intracellular pathways. For example, VEGF, after forming a homodimer, binds to two KDR molecules, for example, at immunoglobulin-like domains Ig2 and Ig3 of KDR. This results in KDR dimerization and activation.

It is widely accepted that tumor growth beyond a few cubic millimeters cannot occur without inducing a new vascular supply. Thus, inhibiting the development of new blood vessels is a potential approach to cancer therapy that has attracted interest in recent years. In view of the role of VEGF in vascular endothelial proliferation and angiogenesis, and the role that these processes play in many different diseases and disorders, it is desirable to have a means for reducing or inhibiting one or more of the biological activities of VEGF. Currently, blockade of the VEGF pathway is achieved by many different means, including blocking antibodies targeted against VEGF or its receptors (Dvorak, HF, *J. Clin. Oncology*, 20: 4368-4380 (2002)), soluble decoy receptors that prevent VEGF from binding to its normal receptors (Kim et al., *PNAS U.S.A.*, 99: 11399-11404 (2002)), and small molecule inhibitors of tyrosine kinase activity of the VEGF receptors.

The present inventors have identified novel compositions and methods for inhibiting VEGF signaling. Thus, the present invention provides a means for reducing or inhibiting endogenous VEGF activity and, in turn, reducing or inhibiting endothelial cell proliferation and angiogenesis.

SUMMARY OF THE INVENTION

The present invention is directed to a VEGF receptor (VEGFR) antagonist that binds to a full length VEGFR monomer and interferes with VEGF signaling. In a preferred embodiment, the VEGF receptor (VEGFR) antagonist comprises immunoglobulin-like domains 4-7, immunoglobulin-like domains 5-7, or functional equivalents thereof. Preferably, the VEGF receptor antagonist comprises at least one immunoglobulin-like domain is from KDR. Still preferred, the VEGF receptor antagonist comprises at least one immunoglobulin-like domains from one VEGF receptor and at least one other immunoglobulin-like domains is from a different VEGFR. Most preferably, the VEGF receptor antagonist is KDR (Ig4-7). The VEGF receptor antagonist may be optionally formulated in a pharmaceutically suitable excipient.

The VEGF receptor antagonists of the present invention may comprise immunoglobulin-like domains selected from the group consisting of kinase domain receptor (KDR), flt-1, flt-4, PDGF, and combinations thereof. Similarly, the VEGF receptor antagonist described herein may form heterodimers with a VEGF receptor selected from the group consisting of kinase domain receptor (KDR), flt-1, flt-4 and PDGF. For example, a VEGFR antagonist that is KDR (Ig4-7) for example, may heterodimerize with a full length VEGFR such as KDR. However, it is contemplated herein that a VEGFR antagonist such as KDR (Ig4-7) may instead heterordimerize with a full-length VEGF receptor that is not KDR.

Also described in the present invention is a fusion protein comprising a VEGF receptor antagonist and at least one domain selected from the group consisting of a prolactin receptor antagonizing domain, a cytokine, a VEGF ligand and a combination thereof. Preferably, the fusion protein comprises a VEGF receptor antagonist and a prolactin receptor antagonizing domain that is G129R. Also preferred, the fusion protein comprises a VEGF receptor antagonist and a VEGF ligand. Still preferred, the fusion protein comprises immunoglobulin-like domains 4-7 or 5-7 or a functional equivalent thereof, from a kinase domain receptor (KDR), flt-1, flt-4, PDGF, and combinations thereof. It is also contemplated that not all immunoglobulin-like domains are selected from a single VEGF receptor. In other words, a chimeric VEGFR antagonist is also contemplated. Most preferably, the fusion protein comprises KDR (Ig4-7) or KDR (Ig5-7).

Also described in the present invention is a polynucleotide encoding a VEGF receptor antagonist that comprises immunoglobulin-like domains 4-7, immunoglobulin-like domains 5-7, or a functional equivalent thereof, from a VEGFR. Preferably, the VEGF receptor is selected from the group consisting of kinase domain receptor (KDR), flt-1, flt-4, PDGF, and combinations thereof. Still preferred, the VEGF receptor antagonist is KDR (Ig4-7). Most preferably, the polynucleotide encodes the protein set forth in SEQ ID NO. 2.

In a related vein, a vector comprising the polynucleotide of the present invention is also described. Similarly, a host cell transformed with the vectors of the present invention are also disclosed. In a preferred embodiment, the host cell is a mammalian host cell.

The present invention further describes a method of treating a cancer, such as breast cancer, or a method of decreasing angiogenesis, comprising: administering a polynucleotide encoding (a) a VEGF receptor antagonist that comprises immunoglobulin-like domains 4-7, immunoglobulin-like domains 5-7, or a functional equivalent thereof, or (b) a fusion protein comprising a VEGF receptor antagonist that comprises immunoglobulin-like domains 4-7 or immunoglobulin-like domains 5-7, and a domain selected from the group consisting of a prolactin receptor antagonizing domain, a VEGF ligand, a cytokine, and a combination thereof. In one embodiment, the fusion protein comprises a prolactin receptor antagonizing domain that is G129R.

Similarly, the present invention describes a method of treating a cancer such as breast cancer, comprising: (i) administering a VEGF receptor antagonist that comprises immunoglobulin-like domains 4-7, immunoglobulin-like domains 5-7, or a functional equivalent thereof, or a fusion protein comprising a VEGF receptor antagonist that comprises immunoglobulin-like domains 4-7 or immunoglobulin-like domains 5-7, and a domain selected from the group consisting of a prolactin receptor antagonizing domain, a VEGF ligand, a cytokine, and a combination thereof; and (ii) inhibiting or substantially inhibiting the VEGF signal transduction cascade.

Also described is a method of decreasing angiogenesis comprising: (i) administering a VEGF receptor antagonist comprising immunoglobulin-like domains 4-7, immunoglobulin-like domains 5-7, or a functional equivalent thereof, or a fusion protein comprising a VEGF receptor antagonist that comprises immunoglobulin-like domains 4-7 or immunoglobulin-like domains 5-7; and (ii) inhibiting formation of tumor neovasculature.

A method for making a VEGF receptor antagonist comprising introducing an expression vector encoding a VEGF receptor antagonist into an appropriate expression system and effecting expression of said VEGF receptor antagonist is also disclosed. Preferably, the VEGF receptor antagonist is KDR (Ig4-7).

Other methods disclosed in the present invention include a method for slowing the progression of a cancer comprising i) administering a VEGF receptor antagonist comprising immunoglobulin-like domains 4-7, immunoglobulin-like domains 5-7, or a functional equivalent thereof, or a fusion protein comprising a VEGF receptor antagonist; and (ii) slowing cell proliferation in the target cell. Preferably, the fusion protein further comprises at least one domain selected from the group consisting of a VEGF ligand, a prolactin receptor antagonizing domain, a cytokine and a combination thereof. Also preferred, the VEGF receptor antagonist comprises at least one immunoglobulin-like domain selected from the group consisting of kinase domain receptor (KDR), flt-1, flt-4, PDGF, and combinations thereof. Most preferably, the VEGF receptor antagonist is a KDR (Ig4-7). The VEGF receptor antagonist of the present method may optionally be formulated in a pharmaceutically suitable excipient.

Also disclosed herein is a cell based assay system for identifying a test compound capable of inducing VEGFR activity, comprising (i) contacting a test compound to a cell that expresses the prolactin receptor, in the presence and absence of a compound that substantially inhibits VEGF mediated cell proliferation, (ii) measuring the level of proliferation in the cell in the presence and absence of the compound that substantially inhibits VEGF mediated cell proliferation, and (iii) comparing the levels of cell proliferation obtained in (ii). In one embodiment, the compound that substantially inhibits VEGF mediated cell proliferation is KDR (Ig4-7), KDR (Ig5-7) or a functional equivalent thereof.

Schematic illustration of the design of KDR (Ig4-7) and G129R-Ig4. The top panel (A) shows the design of five recombinant proteins. The bottom panel (B) shows possible mechanisms of VEGF induced signal transduction (left) and the antagonism of KDR (Ig4-7)(middle) or G129R-Ig4 (right).

Figure 2:
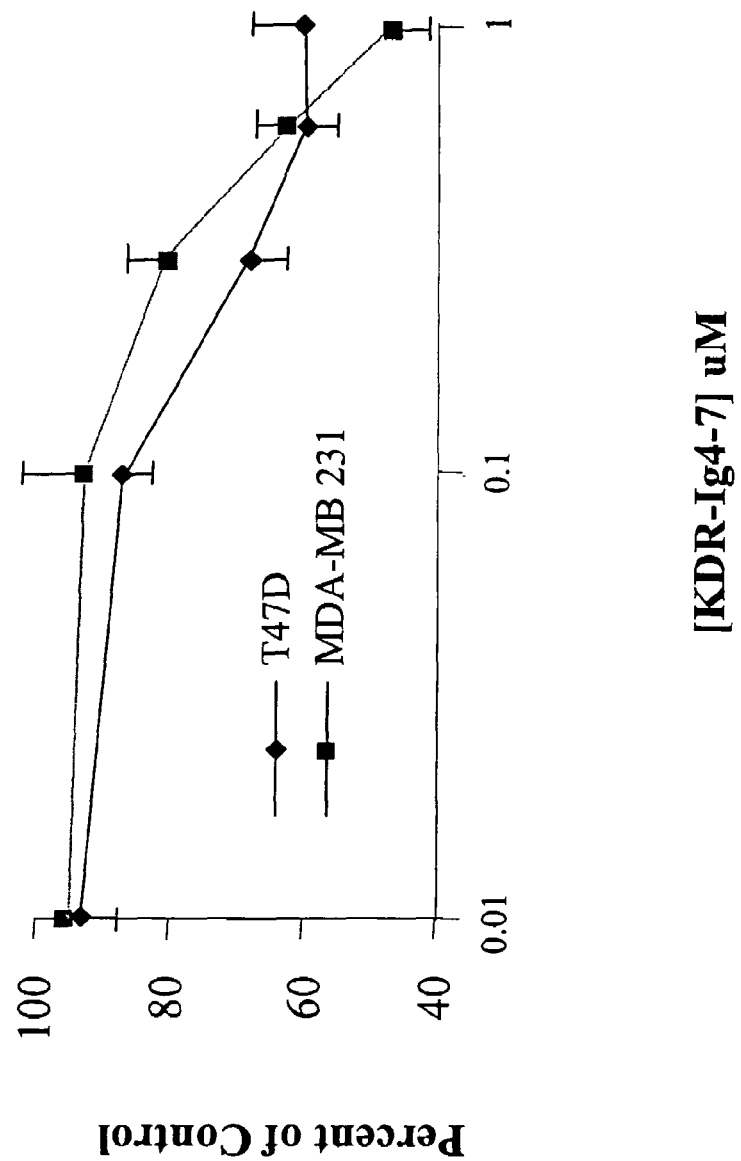

FIG. 2. Cell proliferation assay using two KDR positive human breast cancer cells KDR (Ig4-7) inhibits cell proliferation in T47D and MDA-MB 231 cells in a dose-dependent fashion.

Figure 3:
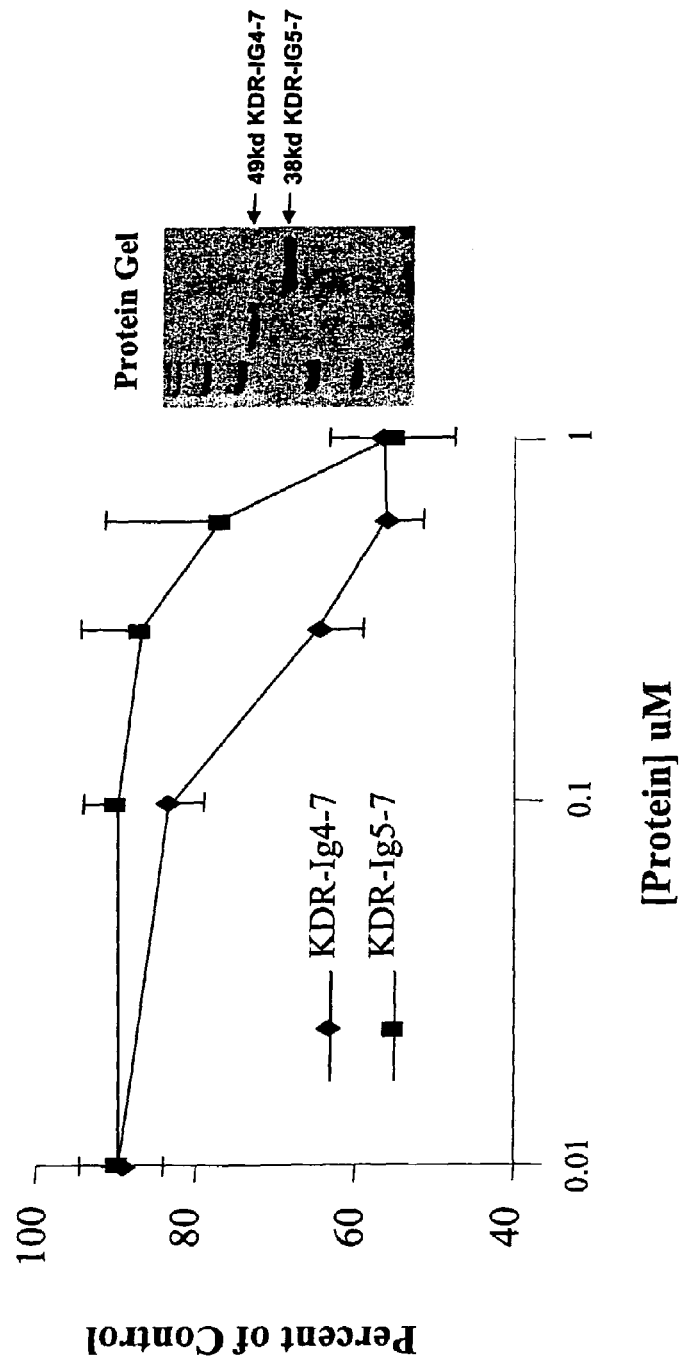

FIG. 3. Comparison of KDR (Ig4-7) and KDR (Ig5-7)

Comparison of the inhibitory effect of KDR (Ig4-7) and KDR (Ig5-7) in inhibition of human breast cancer cell (T-47D) proliferation. Insert: Purified KDR (Ig4-7)(49 Kd) and KDR-Ig-5-7 (38 KD) as shown in staining gel.

Figure 4:
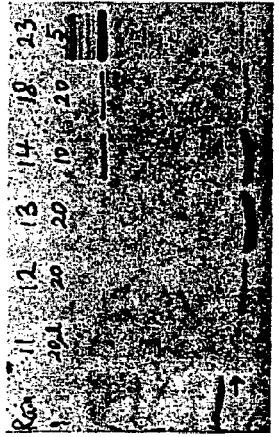
Figure 4:
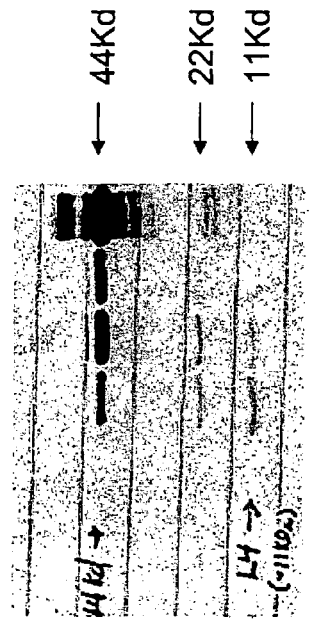

FIG. 4. FPLC Purification (Fractions 11-14, 18, 23)

KDR (Ig4) forms homodimers and tetramers.

Figure 5:
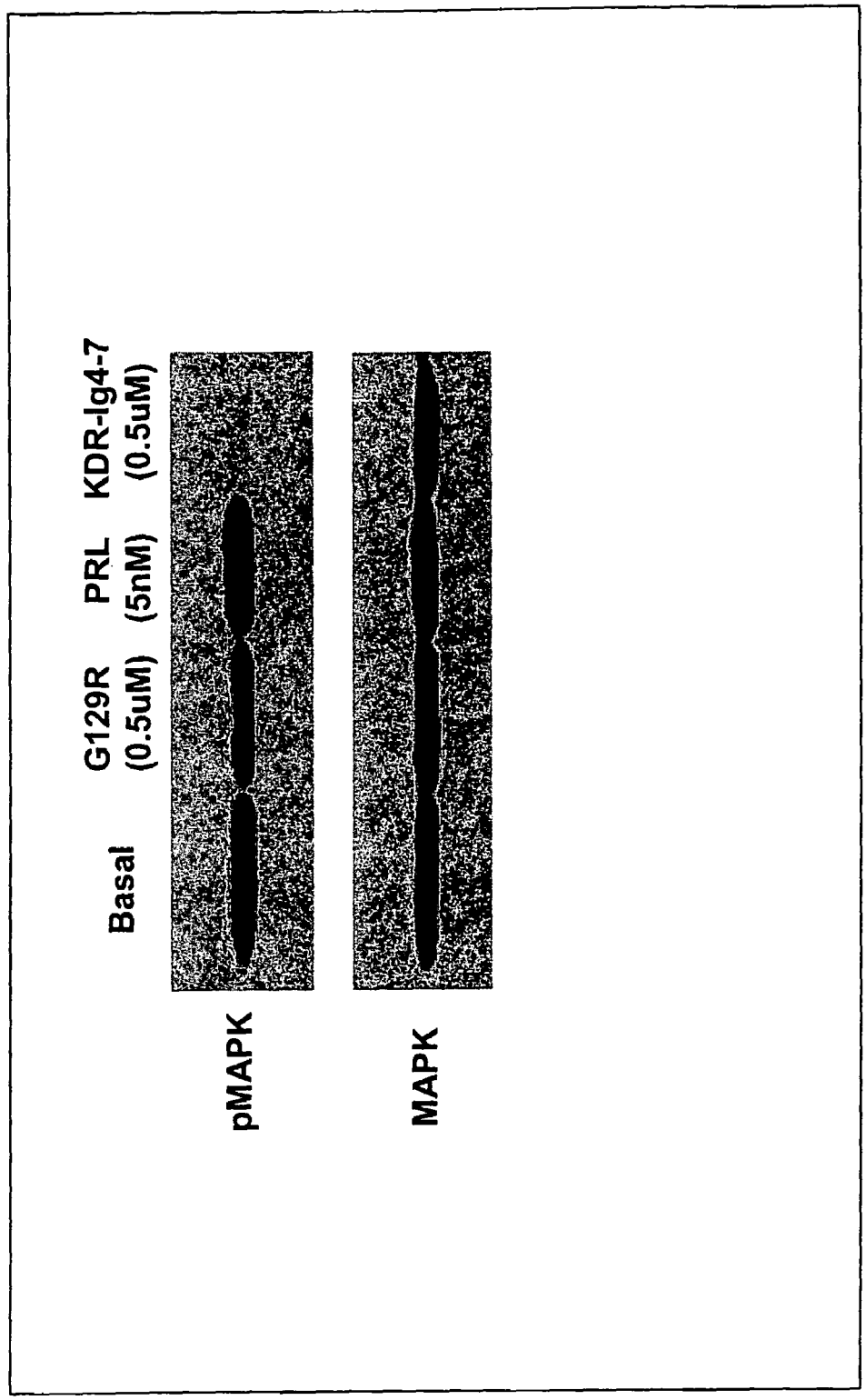

FIG. 5. MAP kinase (MAPK) phosphorylation assay after administration of KDR (Ig4-7)

Inhibition of MAPK phosphorylation by KDR (Ig4-7) using T-47D human breast cancer cells. T-47D cells were cultured overnight in serum free media at 80% confluency and were treated for 60 min with G129R (10 ug/ml, ~0.5 uM); HPRL (100 ng/ml, ~5 nM), and KDR (Ig4-7)(25 ug/ml, ~0.5 uM) as compared to untreated cells (basal). Membranes were stripped and re-probed with anti-MAPK antibody to ensure equal loading.

Figure 6:
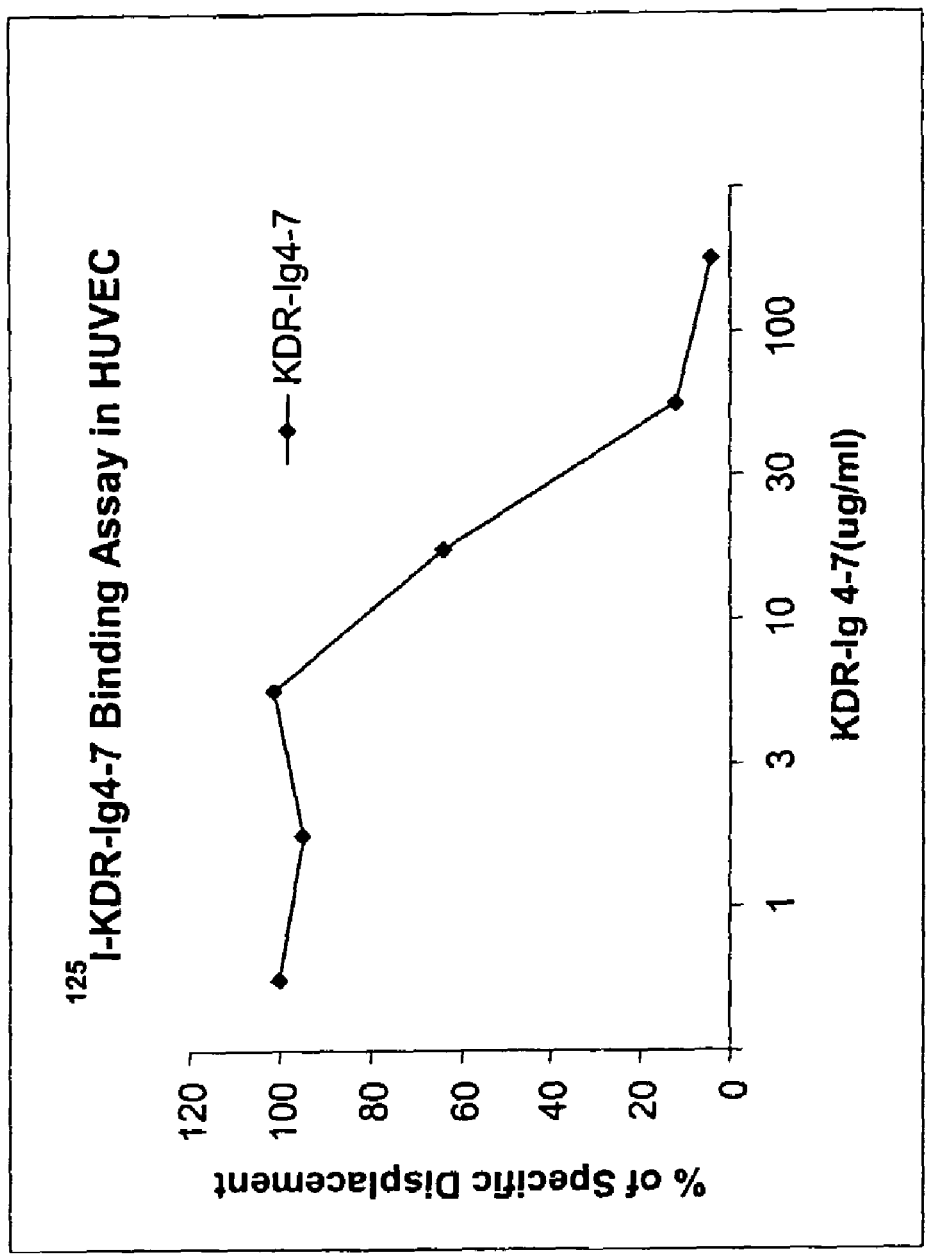

FIG. 6. KDR (Ig4-7) binding assay $^{125}$I-KDR (Ig4-7) (100,000 cpm=<1 ng) was incubated with HUVEC. Results indicate that increasing concentrations of unlabeled KDR (Ig4-7) displaced radiolabeled KDR (Ig4-7), thereby confirming binding specificity of the VEGF receptor antagonist.

Figure 7:
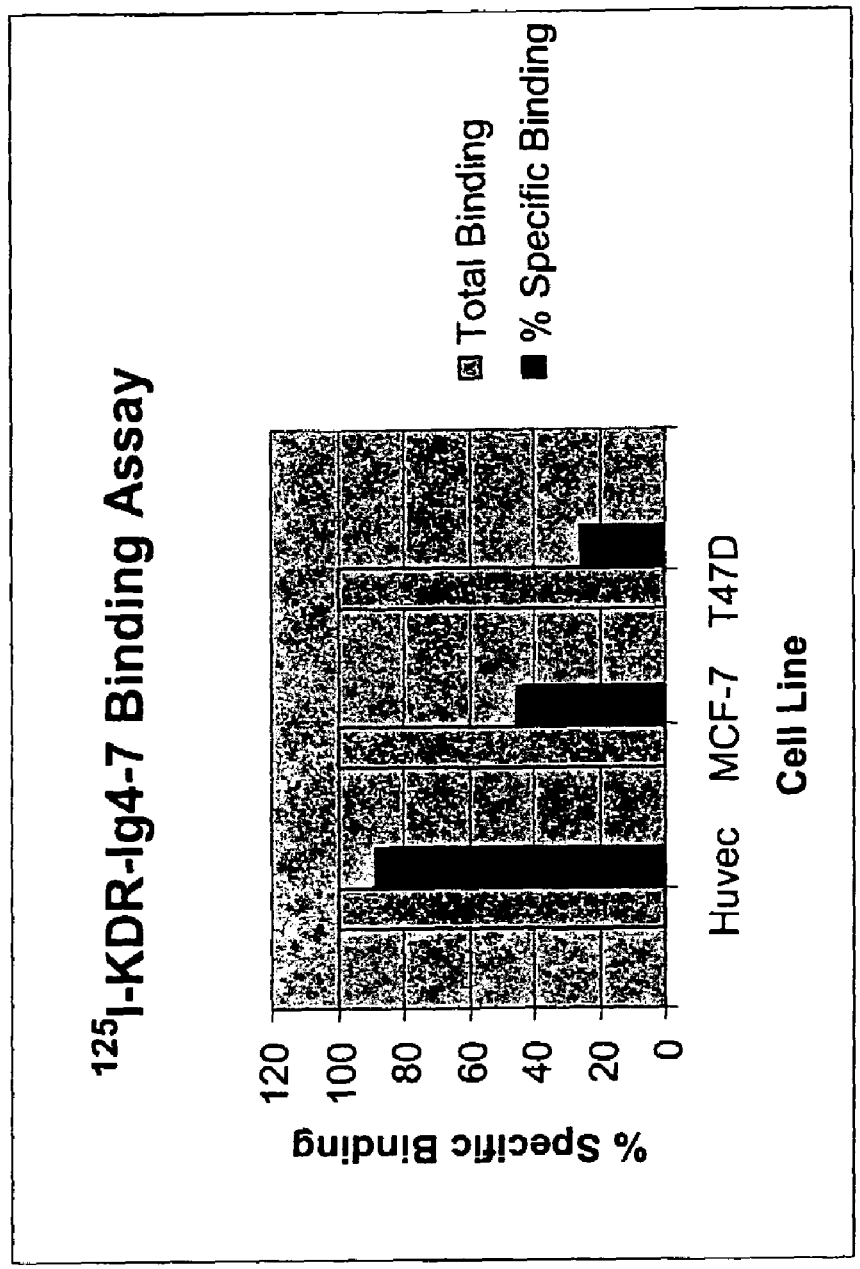

FIG. 7. $^{125}$I-KDR (Ig4-7) binding assay in multiple cell lines

KDR (Ig4-7) binding in HUVEC, L-cells, MCF-7 and T47-D cell lines was assessed.

FIG. 8. KDR (Ig4-7) sequences
(A) cDNA (SEQ ID NO. 1) and (B) amino acid sequence (SEQ ID NO. 2) information for KDR (Ig4-7).

FIG. 9. KDR (Ig4-7) with partial Ig4 sequence
(A) cDNA (SEQ ID NO. 3) and (B) amino acid sequence (SEQ ID NO. 4) information for KDR (Ig4-7) which contains a partial Ig4 sequence.

DETAILED DESCRIPTION OF THE PREFERRED EMBODIMENTS

Introduction

KDR is characterized as a transmembrane tyrosine kinase receptor of sub-type 5 which serves as a key regulator of vascular endothelial cell development during embryogenesis and cell regeneration (*Cancer and Metastasis Reviews*, 15: 159-163 (1996)). The full length KDR receptor binds the VEGF protein with high affinity via its extracellular domain, which is comprised of seven immunoglobulin-like domains (Ig1-7). The first three (Ig1-3) domains are thought to be required for VEGF binding, Ig4 region is believed to be responsible for receptor dimerization and Ig7 prevents receptor dimerization in the absence of a VEGF ligand.

The present invention describes a novel class of angiogenesis inhibitors targeting VEGFRs. The design is based on the inventors' unexpected experimental results using a portion of the extracellular domain of KDR. Surprisingly, the inventors determined that a fragment of the KDR extracellular domain that contains four Ig regions (KDR-Ig4-7), but lacks VEGF binding domains (regions 2 and 3), is able to inhibit human umbilical vein endothelial cells (HUVEC) and KDR positive breast cancer cell proliferation. The inventors have further shown that the inhibitory effect of KDR (Ig4-7) is, at least in part, due to the inhibition of MAPK phosphorylation (FIG. 5).

While not wishing to be bound to a particular theory, the inventors hypothesize that the VEGF receptor (VEGFR) antagonists of the present invention bind a full length VEGF receptor monomer, and therefore reduce the number of available full length receptor monomers that normally homodimerize in the presence of a ligand. As a result, VEGF signaling is impaired.

In the specific case of KDR, the inventors hypothesize that a soluble form of KDR, such as KDR (Ig4-7), is capable of binding to a cell surface KDR via its dimerization domain (located mainly in Ig4) and forming a KDR/KDR (Ig4-7) complex. This KDR/KDR (Ig4-7) dimer is a non-functional complex and therefore, interferes with VEGF cell signaling. Thus, KDR (Ig4-7) serves as a VEGFR antagonist.

Definitions

As used herein, the term "VEGF receptor antagonist" means a receptor molecule having amino acid sequences derived from at least one different protein, said receptor antagonist being capable of inhibiting the activity of VEGF (or VEGF homologs). Preferably, the VEGF receptor antagonist of the present invention consist of an amino acid sequence derived at least from a KDR molecule, however, the VEGF receptor antagonist may be derived from the extracellular region of the flt-1 receptor, flt-4 receptor, or a combination thereof. For example, the VEGF receptor antagonist may be a chimeric protein that comprises an Ig-like region from one VEGF receptor and another Ig-like domain from a different VEGF receptor.

"Immunoglobulin-like domain" or "Ig-like domain" refers to each of the seven independent and distinct domains that are found in the extracellular ligand-binding region of the flt-1, KDR and flt-4 receptors. PlGF is also part of the VEGF superfamily. Ig-like domains are generally referred to by number (e.g., Ig 1 or Ig2), the number designating the specific domain as it is shown in FIG. 1A. As used herein, the term "Ig-like domain" or "Ig" followed by a number, is intended to encompass not only the wild-type domain (either a complete or portion of the wild-type domain), but also insertional, deletional and substitutional and other modified variants thereof which substantially retain the functional characteristics of the wild-type domain.

"Functional equivalent" when used in reference to the Ig-like domains of the extracellular ligand-binding regions of the flt-1, KDR or flt-4 receptors means the Ig-like domain or domains possess at least one particular alteration, such as a modification (e.g., covalent modification, hydroxylation, phosphorylation, methylation, acetylation and amidation), deletion, addition and/or substitution therein yet retains substantially the same functional characteristics as does the wild type Ig-like domain or domains. For example, a functional equivalent of a VEGF receptor antagonist that comprises Ig4-7 may be a VEGF receptor antagonist that comprises only a portion of Ig4 (i.e., a partial Ig4 sequence) and Ig5-7, provided that the functional equivalent has substantially the same activity as the VEGF receptor antagonist. The VEGF receptor antagonist and functional equivalents thereof decrease cell proliferation and/or vascularization and/or angiogenesis. One of ordinary skill in the art can readily test the activity of a potential VEGF receptor antagonist by, for example, standard cell proliferation assays.

"Inhibitory effect" when used in reference to the activity of a VEGF receptor antagonist of the present invention means that the VEGF receptor antagonist is capable of binding to a full length VEGF receptor and inhibiting or substantially inhibiting the activity of VEGF (or a VEGF homolog) by forming a non-functional multimeric, and preferably heterodimeric, complex. Generally, the result of this inhibitory effect is a decrease in the vascularization and/or angiogenesis which occurs as a result of VEGF signaling.

"Undesired vascularization" refers to the endothelial proliferation and/or angiogenesis which is associated with an undesirable disease or disorder and which, if reduced or eliminated, would result in a reduction or elimination of the undesirable characteristics of the disease or disorder. For example, the vascularization and/or angiogenesis associated with tumor formation and metastasis and various retinopathies is undesirable.

Composition

The compositions of the present invention can be used in combination with other therapeutic agents, such as cytokines, various chemotherapeutic compounds and other agents for cancer treatment.

VEGF Receptor Antagonists

Contemplated in the present invention is a VEGF receptor antagonist comprising a VEGF receptor (VEGFR) that comprises immunoglobulin-like domains 4-7 and therefore interferes with VEGF signaling. Preferably, the VEGF receptor is selected from the group consisting of KDR, VEGFR1 (flt-1), VEGFR3 (flt-4) and PDGF. Still preferred, the VEGF receptor is KDR and the VEGF receptor antagonist comprises KDR (Ig4-7) or KDR (Ig5-7) or functional equivalents thereof.

In a related vein, the present invention describes a VEGF receptor antagonist that comprises Ig-like domains 5-7 or a VEGF receptor antagonist that comprises Ig-like domains 5-7 and all or a portion of Ig-like domain 4.

Also contemplated in the present invention is a chimeric VEGF receptor antagonist. For example, a VEGF receptor antagonist (Ig4-7) may comprise Ig4 from VEGFR1 and Ig5-7 from KDR. Likewise, the present invention contemplates a chimeric VEGFR antagonist that comprises Ig4 from VEGFR1, a second Ig4 from VEGFR2, and Ig5-7 from VEGFR1 or VEGFR2. Other permutations among the different VEGF receptor antagonists are, based on the teachings of the instant specification, within the purview of one of ordinary skill in the art. The activity of the VEGFR antagonist can then be easily assayed by known techniques.

The VEGF receptor antagonists of the present invention bind few, if any, other VEGF receptor antagonists. In other words, the VEGF receptors will preferably not homodimerize or form dimers with other VEGF receptors. For example, very few KDR (Ig4-7) proteins will bind, if at all, other KDR (Ig4-7) proteins.

The Ig4 domain of the VEGF receptor is thought to be important in VEGF receptor dimerization. However, a VEGFR (Ig4) alone forms a relatively large number of homodimers and is not suitable for use in the present invention (FIG. 4). Indeed, it is less preferably to use a VEGF receptor (Ig4), such as KDR (Ig4), to interfere with VEGF signaling because KDR (Ig4) will predominantly form homodimers and tetramers, independent of ligand binding. This is in contrast with VEGF receptor (Ig4-7), for example, which will preferentially form heterodimers with a full length KDR.

Figure 1:
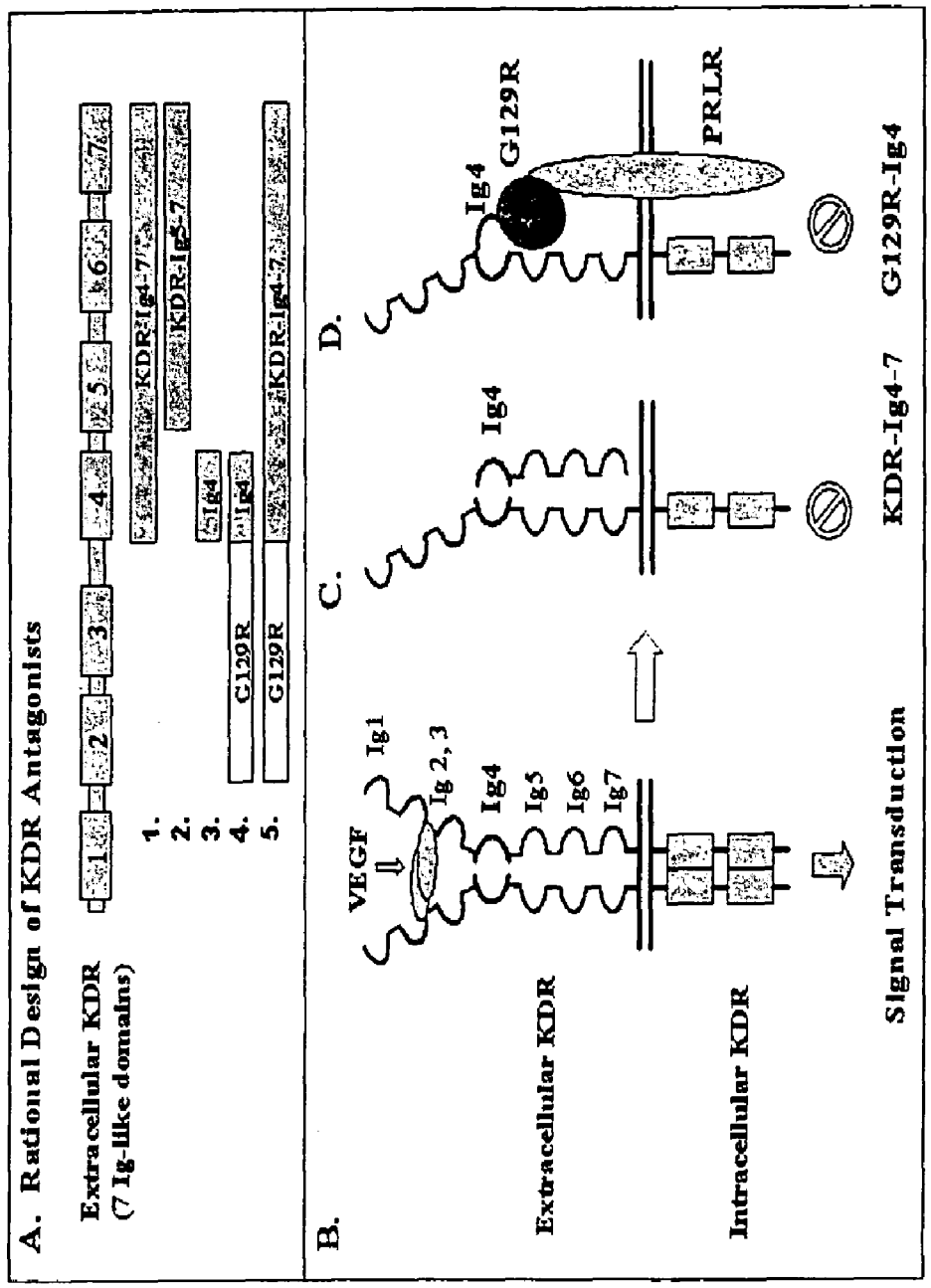
FIG. 1. Illustration of KDR antagonists

Interestingly, a fusion protein comprising VEGF receptor (Ig4) and a prolactin antagonizing domain such as G129R interferes with VEGF signaling and is therefore also a VEGF receptor antagonist (FIG. 1).

Additionally, the VEGF receptor antagonists of the present invention are able to heterodimerize with a full length KDR, even in the absence of ligand binding. This is surprising because domain 7 is important for preventing dimerization of a full-length KDR with another full length receptor in the absence of a ligand. Normally, a full-length KDR will not homodimerize in the absence of a ligand if domain 7 is intact (Tao et al., *J. Biol. Chem.*, 276:21916-21923 (2001)). This is in contrast with the VEGFR antagonists of the present invention, namely KDR antagonists, which retain the ability to dimerize in the absence of a VEGF ligand even though the KDR antagonist contains domain 7. As such, KDR (Ig4-7), KDR (Ig5-7) and functional equivalents thereof can dimerize with a full length KDR independent of ligand binding.

Also described herein is a polynucleotide encoding a VEGF receptor antagonist that comprises a VEGF receptor comprising immunoglobulin-like domains 4-7, or immunoglobulin-like domains 5-7 that optionally comprise a partial Ig4 sequence. In a preferred embodiment, the polynucleotide encodes a VEGF receptor selected from the group consisting of KDR, VEGFR1, VEGFR3 and PDGF. Most preferably, the polynucleotide encodes the amino acid sequence set forth in SEQ ID No. 2. or 4.

Conservative variants of the polynucleotides and proteins of the present invention are also contemplated. The conservative variants according to the invention generally preserve the overall molecular structure of the protein domains. Given the properties of the individual amino acids comprising the disclosed protein products, some rational substitutions will be apparent. Amino acid substitutions, i.e. "conservative substitutions," may be made, for instance, on the basis of similarity in polarity, charge, solubility, hydrophobicity, hydrophilicity, and/or the amphipathic nature of the residues involved.

For example: (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt α-helices. Similarly, certain amino acids, such as alanine, cysteine, leucine, methionine, glutamic acid, glutamine, histidine and lysine are more commonly found in α-helices, while valine, isoleucine, phenylalanine, tyrosine, tryptophan and threonine are more commonly found in β-pleated sheets. Glycine, serine, aspartic acid, asparagine, and proline are commonly found in turns. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants.

Conservative variants specifically contemplate truncations of the presently described receptor antagonizing domains. Truncations may be made from the N- or C-terminus, but generally do not entail deleting more than about 30% of the native molecule. More preferably, less than about 20%, and most preferably, less than about 10%, of the native molecule is deleted.

In general, both the DNA and protein molecules of the invention can be defined with reference to "sequence identity." Some molecules have at least about 50%, 55% or 60% identity. Preferred molecules are those having at least about 65% sequence identity, more preferably at least 70% sequence identity. Other preferred molecules have at least about 80%, more preferably at least 85%, sequence identity. Most preferred molecules have at least about 90%, more preferably at least 95%, sequence identity. As used herein, two nucleic acid molecules or proteins are said to "share significant sequence identity" if the two contain regions which possess greater than 85% sequence (amino acid or nucleic acid) identity.

"Sequence identity" is defined herein with reference the Blast 2 algorithm, which is available at the NCBI (www.ncbi.nlm.nih.gov/BLAST), using default parameters. References pertaining to this algorithm include: those found at www.ncbi.nlm.nih.gov/BLAST/blast_references.html; Altschul et al., *J. Mol. Biol.*, 215: 403-410 (1990); Gish, W. & States, D. J, *Nature Genet.*, 3: 266-272 (1993); Madden et al., *Meth. Enzymol.* 266: 131-141 (1996); Altschul et al., *Nucleic Acids Res.*, 25: 3389-3402 (1997); and Zhang, J. & Madden, T. L., *Genome Res.* 7: 649-656 (1997). Accordingly, the prolactin peptide sequences from different species, which include those listed in Table 1, can be aligned, using standard computer programs like BLAST, to inform further variation in prolactin-derived receptor-antagonizing domains that preserve their essential function.

Fusion Proteins

The present invention also contemplates a fusion protein that comprises a VEGF receptor antagonist. The fusion protein may further comprise at least one of the following: a cytokine or other therapeutic agent, a prolactin receptor antagonist, a VEGF ligand, or another agent that will aid in targeting the fusion protein to a target cell.

In one embodiment, the fusion proteins of the instant invention comprise (1) a VEGF receptor antagonist and (2) a prolactin receptor antagonizing domain, wherein upon such fusing, both domains substantially retain their associated characteristics, independent of the other. FIG. 1B illustrates one embodiment of the invention, according to these characteristics.

In a preferred embodiment, the prolactin receptor antagonizing domain is G129R. This prolactin receptor antagonist is described in U.S. patent application Ser. No. 09/815,306, entitled "Bi-functional cancer treatment agents," which is incorporated herein by reference in its entirety.

Also contemplated in the present invention is a fusion protein comprising (1) a VEGF receptor antagonist and (2) and a VEGF ligand, wherein upon such fusing, both domains substantially retain their associated characteristics, independent of the other.

An additional advantage of the fusion protein is that it provides a method for increasing the ability of either the KDR antagonist or the prolactin receptor antagonist to target a cancer cell, such as a breast cancer cell. For example, G129R has an affinity for the prolactin receptor and therefore, G129R will target a cell that expresses a prolactin receptor. Likewise, the KDR antagonist has an affinity for KDR and will therefore target a cell that expresses KDR. Thus, a cell that expresses both KDR and prolactin can be targeted by two means as opposed to just one. In other words, the KDR antagonist part of the fusion protein will be attracted to a cell expressing KDR and G129R part of the fusion protein will be attracted to the same cell that also expresses a prolactin receptor. Accordingly, the targeting ability of a G129R-KDR (Ig4-7) fusion protein may be greater than the targeting ability of either domain alone.

Suitable methods for creating the fusion protein should be ones that do not substantially change the biological activity of either domain. This process includes designing a cDNA encoding a fusion protein which links the N-terminus of the VEGF receptor antagonist to the C-terminus of prolactin receptor antagonizing domain and/or VEGF ligand. Although typically produced as fusion proteins, the domains also may be fused by conventional chemical means, using multifunctional cross-linkers, for example. When fusion proteins are made, either domain may be placed C-terminal or N-terminal to the other.

The present invention is not limited to any particular method of producing the desired fusion protein contemplated herein. According to the contemplated recombinant methods of production, however, the invention provides recombinant DNA constructs comprising one or more of the nucleotide sequences of the VEGF receptor antagonist described in the present invention. The recombinant constructs of the present invention comprise a vector, such as a plasmid or viral vector, into which a DNA or DNA fragment, typically bearing an open reading frame, is inserted, in either orientation. The invention further contemplates cells containing these vectors.

The term "expression vector" refers to an oligonucleotide which encodes the peptide of the invention and provides the sequences necessary for its expression in the selected host cell. Expression vectors will generally include a transcriptional promoter and terminator, or will provide for incorporation adjacent to an endogenous promoter. Expression vectors will usually be plasmids, further comprising an origin of replication and one or more selectable markers. However, expression vectors may alternatively be viral recombinants designed to infect the host, or integrating vectors designed to integrate at a preferred site within the host's genome. Examples of viral recombinants are Adeno-associated virus (AAV), Adenovirus, Herpesvirus, Poxvirus, Retrovirus, and other RNA or DNA viral expression vectors known in the art. Examples of other expression vectors are disclosed in Sambrook, Fritsch, and Maniatis, MOLECULAR CLONING: A LABORATORY MANUAL, 2nd Edition, Cold Spring Harbor Laboratory Press, N.Y. (1989).

Described herein is a polynucleotide encoding a VEGF receptor antagonist and a prolactin receptor antagonizing domain and/or a VEGF ligand. Such a polynucleotide can be integrated into an expression vector, which can then be transfected into a stable cell line to subsequently produce a purified protein.

Therefore, the present invention contemplates a DNA construct comprising a nucleotide sequence of a VEGF receptor antagonist of the present invention. In a preferred embodiment, VEGF receptor antagonist comprises a VEGF receptor (VEGFR) that consists essentially of immunoglobulin-like domains 4-7. Also preferred, the VEGF receptor is selected from the group consisting of kinase domain receptor (KDR), VEGFR1, VEGFR3 and PDGF. Most preferably, the DNA construct of the present invention comprises a nucleic acid sequence of a KDR receptor antagonist. Still preferred, the VEGF receptor antagonist nucleotide sequence encodes the amino acid sequence set forth in SEQ ID NO. 2 or 4.

The vectors and methods disclosed herein are suitable for use in host cells over a wide range of prokaryotic and eukaryotic organisms. In general, of course, prokaryotes are preferred for the initial cloning of DNA sequences and construction of the vectors useful in the invention.

Prokaryotes may also be used for expression. Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and, if desirable, to provide amplification within the host. Suitable prokaryotic hosts for transformation include *E. coli, Bacillus subtilis, Salmonella typhimurium* and various species within the genera *Pseudomonas, Streptomyces,* and *Staphylococcus,* although others may, also be employed as a matter of choice. In a preferred embodiment, the prokaryotic host is, but not limit to, BL21 derivatives.

Bacterial vectors may be, for example, bacteriophage-, plasmid- or cosmid-based. These vectors can comprise a selectable marker and bacterial origin of replication derived from commercially available plasmids typically containing elements of the well known cloning vector pBR322 (ATCC 37017). Such commercial vectors include, for example, GEM 1 (Promega Biotec, Madison, Wis., USA), pBs, phagescript, PsiX174, pBluescript SK, pBs KS, pNH8a, pNH16a, pNH18a, pNH46a (Stratagene); pTrc99A, pKK223-3, pKK233-3, pKK232-8, pDR540, and pRIT5 (Pharmacia). A preferred vector according to the invention is from Novagen, pET22b.

These "backbone" sections are combined with an appropriate promoter and the structural sequence to be expressed. Bacterial promoters include lac, T3, T7, lambda $P_R$ or $P_L$, trp, and ara. is the preferred bacterial promoter. While these are the most commonly used, other microbial promoters have been discovered and utilized, and details concerning their nucleotide sequences have been published, enabling a skilled worker to ligate them functionally with plasmid vectors (see, e.g., Siebenlist et al., *Cell,* 20, 269 (1980)).

In addition to prokaryotes, eukaryotic microbes, such as yeast cultures, may also be used. *Saccharomyces cerevisiae,* or common baker's yeast, is the most commonly used among eukaryotic microorganisms, although a number of other strains are commonly available. For expression in *Saccharomyces,* the plasmid YRp7, for example (Stinchcomb et al.,

*Nature* 282:39-43 (1979); Kingsman et al., *Gene,* 7:141-52 (1979); Tschumper et al., *Gene,* 10:157-66 (1980)), is commonly used. This plasmid already contains the trp1 gene that provides a selection marker for a mutant strain of yeast lacking the ability to grow in tryptophan, for example, ATCC No. 44,076 or PEP4-1 (Jones, *Genetics,* 85:23-33 (1977)). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., *J. Biol. Chem.* 255: 2073 (1980)) or other glycolytic enzymes (Hess et al., *J. Adv. Enzyme Reg.* 7:149 (1968); Holland et al., *Biochemistry,* 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions, are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

Following transformation of a suitable host strain and growth of the host strain to an appropriate cell density, the selected promoter is derepressed/induced by appropriate means (e.g., temperature shift or chemical induction) and cells are cultured for an additional period. Cells are typically harvested by centrifugation, disrupted by physical or chemical means, and the resulting crude extract retained for further purification.

Various mammalian cell culture systems can also be employed to express recombinant protein. Examples of mammalian expression systems include selected mouse L cells, such as thymidine kinase-negative (TK) and adenine phosphoribosul transferase-negative (APRT) cells. Other examples include the COS-7 lines of monkey kidney fibroblasts, described by Gluzman, *Cell,* 23: 175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking non-transcribed sequences. DNA sequences derived from the SV40 viral genome, for example, SV40 origin, early promoter, enhancer, splice, and polyadenylation sites may be used to provide the required non-transcribed genetic elements.

Mammalian promoters include CMV immediate early, HSV thymidine kinase, mouse mammary tumor virus, early and late SV40, LTRs from retrovirus, and mouse metallothionein-I. Exemplary mammalian vectors include pWLneo, pSV2cat, pOG44, pXT1, pSG (Stratagene) pSVK3, pBPV, pMSG, and pSVL (Pharmacia).

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a target protein in infected hosts (see, e.g., Logan et al., *PNAS U.S.A.,* 81: 3655-3659 (1984)).

Pharmaceutical Excipients

The proteins of the present invention can be formulated according to known methods to prepare pharmaceutically useful compositions, whereby the inventive molecules, or their functional derivatives, are combined in admixture with a pharmaceutically acceptable carrier vehicle. Suitable vehicles and their formulation, inclusive of other human proteins, e.g., human serum albumin, are described, for example, in *Remington's Pharmaceutical Sciences* (16th ed., Osol, A., ed., Mack, Easton Pa. (1980)). To form a pharmaceutically acceptable composition suitable for effective administration, such compositions will contain an effective amount of one or more of the proteins of the present invention, together with a suitable amount of carrier vehicle.

The compositions for use in accordance with the present invention may be formulated in conventional manner using one or more physiologically acceptable carriers or excipients. Thus, the may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they maybe presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the composition may take the form of tablets or lozenges formulated in conventional manner.

For administration by inhalation, the VEGF receptor antagonists and fusion proteins according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g. gelatin for use in an inhaler or insufflator may be formulated containing a powder mix of the compound and a suitable powder base such as lactose or starch.

The fusion proteins and VEGF receptor antagonists of the present invention may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the fusion proteins and VEGF receptor antagonists of the present invention may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Cell-Based Assays

The present invention also provides a cell-based assay system that can be used to identify compounds or compositions that inhibit VEGF signaling, and therefore, may be useful for regulation of cell proliferation and treatment of diseases or disorders associated with undesirable vascularization. The assay system is based on the observation that VEGF receptor antagonists (Ig4-7) and (Ig5-7) are capable of substantially inhibiting the effect of VEGF.

In accordance with the present invention, a cell-based assay system is provided to screen for compounds that modulate the activity of a VEGF receptor, and thereby modulate cell proliferation and/or vascularization. Compounds that may affect VEGFR activity include but are not limited to compounds that bind to a VEGFR monomer and either activate signal transduction (agonists) or block activation (antagonists). The invention assay systems provide rapid, reliable methods for identifying compounds which interact with, and thereby affect the function of the VEGFR.

As such, the present invention describes a method for identifying a compound capable of modulating VEGFR activity comprising (i) contacting a compound to a cell that expresses a VEGFR, (ii) measuring the level of cell proliferation in a cell, and (iii) comparing the level of cell proliferation obtained in (ii) to the level obtained in the absence of the test compound, such that if the level obtained in (ii) differs from that obtained in the absence of a compound, a compound is capable of modulating VEGFR activity has been identified.

In yet another embodiment of the invention, a method for identifying a compound capable of inducing VEGFR activity is provided, comprising (i) contacting a test compound to a cell that expresses the prolactin receptor, in the presence and absence of a compound that substantially inhibits VEGF mediated cell proliferation (such a KDR (Ig4-7) or KDR (Ig5-7)), (ii) measuring the level of proliferation in the cell in the presence and absence of the compound that substantially inhibits VEGF mediated cell proliferation, and (iii) comparing the levels of cell proliferation obtained in (ii), such that if the level of proliferation has increased, a compound capable of inducing the activity of the VEGFR has been identified. Assays for measuring cell proliferation are known in the art.

To this end, cells that endogenously express a VEGFR can be used to screen for compounds that modulate the activity of the receptor. In a preferred embodiment, the cells are transformed cells, such as for example, breast cancer cells. In addition, cells that do not normally express VEGFR can be genetically engineered to express a VEGFR gene and such cells may be used for screening purposes. Those of skill in the art recognize that any cell line capable of transfection and having low or no background level of VEGFR is acceptable.

The ability of a test compound to inhibit or substantially inhibit cell proliferation more than those levels seen with cells treated with a vehicle control indicates that the test compound acts as an antagonist to inhibit signal transduction mediated by a VEGFR. In contrast, the ability of a test compound to enhance cell proliferation in the presence of a compound such as a VEGFR antagonist, above those levels seen with cells treated with a vehicle control, indicates that the test compound induces signal transduction mediated by VEGFR.

Methods

Method of Treatment

For therapeutic applications, the VEGF receptor antagonists of the present invention are administered to a mammal, preferably a human, in a pharmaceutically acceptable dosage form, including those that may be administered to a human intervenously as a bolus or by continuous infusion over a period of time, by intramuscular, intraperitoneal, intracerebrospinal, subcutaneous, intra-arterial, intrasynovial, intrathecal, oral, topical, or inhalation routes. The VEGF receptor antagonists of the present invention are also suitably administered by intratumoral, peritumoral, intralesional or perilesional routes, to exert local as well as systemic effects. The intraperitoneal route is expected to be particularly useful, for example, in the treatment of various cancers and metastatic lesions.

Contemplated in the present invention is a method of slowing the progression of a cancer comprising (i) administering a VEGF receptor antagonist and (ii) optionally formulating the VEGF receptor antagonist in a pharmaceutically acceptable excipient. In one embodiment, the VEGF receptor antagonist does not have a ligand binding domain but retains its receptor interaction domain. Preferably, the VEGF receptor antagonist comprises a VEGF receptor that consists essentially of immunoglobulin-like domains 4-7 or Ig5-7 and optionally comprises a partial Ig4 sequence. Also preferred, the VEGF receptor antagonist may be a chimeric protein that comprises an Ig-like region from one VEGF receptor and another Ig-like domain from a different VEGF receptor. Still preferred, the VEGF receptor antagonist is selected from the group consisting of KDR (Ig4-7), KDR (Ig5-7), flt-1 (Ig4-7), flt-4 (Ig4-7) and PDGF (Ig4-7). Most preferably, the VEGF receptor is encoded by SEQ ID No. 1 or 3.

Thus, in one embodiment, the present invention is directed to a method of treatment whereby a VEGF receptor antagonist is administered, unfused to another domain. The VEGF receptor antagonist can heterodimerize with a VEGF receptor monomer, thereby decreasing the number of VEGF receptors available for VEGF signaling. However, in one embodiment, the VEGF ligand binds to the VEGF receptor antagonist. Since the VEGF receptor antagonist forms a non-functional complex, VEGF signaling is still inhibited.

Also contemplated in the present invention is a method of slowing the progression of a cancer comprising (i) administering a fusion protein comprising a VEGF receptor antagonist and (ii) optionally formulating the VEGF receptor antagonist in a pharmaceutically acceptable excipient. Preferably, the fusion protein comprises a VEGF receptor antagonist and (i) a prolactin receptor antagonizing domain and/or (ii) a VEGF ligand. Preferably, the VEGF receptor antagonist is selected from the group consisting of KDR (Ig4-7), KDR (Ig5-7), flt-1 (Ig4-7), flt-4 (Ig4-7) and PDGF (Ig4-7).

Thus, the inventive therapeutic methods according to the invention utilize fusion proteins that comprise a VEGF receptor antagonist. As discussed supra, the VEGF receptor antagonist preferably antagonizes a VEGF receptor selected from the group consisting of KDR, flt-1, flt-4 and PDGF. More preferably, the VEGF receptor antagonist consists essentially of immunoglobulin-like domains 4-7. Most preferably, the VEGF receptor antagonist is KDR (Ig4-7).

For example, KDR (Ig4-7) or KDR (Ig5-7) fused to a prolactin receptor antagonizing domain, such as the human prolactin receptor antagonist, G129R, can be used as a breast cancer therapeutic. A G129R-KDR (Ig4-7) or G129R-KDR (Ig5-7) fusion protein will possess two binding sites: a first site that binds to a prolactin receptor with known high affinity and a second site that binds to KDR. The dual binding ability of the fusion protein to two co-expressed receptors on a breast cancer cell will form a non-functional hetero-dimer of PRLR and KDR and therefore, block both receptors. Since both KDR and the prolactin receptor (PRLR) are up-regulated in breast cancer cells and are thought to contribute to tumor progression, the present invention provides an innovative class of tumor therapeutics that uniquely block cell signaling. The domains of the fusion proteins share the ability to specifically target a tissue, such as breast tissue, and interfere with VEGF and/or prolactin cell signaling in the targeted tissue.

Similarly, the fusion proteins of the present invention may comprise a VEGF receptor antagonist and at least one cytokine such as IL-2 or IL-12.

Without wishing to be bound to any theory, it is believed that a soluble VEGF receptor antagonist comprising immunoglobulin-like domains 4-7 is capable of targeting a cell surface VEGF receptor through its dimerization domain (Ig4). For example, soluble KDR (Ig4-7) may bind to a cell surface KDR receptor monomer, forming a KDR/KDR (Ig4-7) heterodimer. The "crippled" KDR/KDR (Ig4-7) dimer is a non-functional complex that blocks KDR signal transduction. Thus, KDR (Ig4-7) is a VEGF receptor antagonist, namely, a KDR antagonist. Likewise, KDR (Ig5-7) is also a VEGF receptor antagonist and is therefore capable of interfering with VEGF signaling.

Also described herein is a method of treating a cancer or decreasing angiogenesis comprising administering a polynucleotide encoding (a) a VEGF receptor antagonist comprising or (b) a fusion protein comprising a VEGF receptor antagonist. Preferably, the VEGF receptor antagonist antagonizes a VEGF receptor selected from the group consisting of KDR, flt-1, flt-4 and PDGF. More preferably, the VEGF receptor antagonist consists essentially of immunoglobulin-like domains 4-7. Still preferred, the VEGF receptor antagonist is KDR (Ig4-7). Most preferably, the VEGF receptor is encoded by SEQ ID NO. 1. Also preferred, the fusion protein comprises a VEGF receptor antagonist and a prolactin receptor antagonizing domain, such as G129R, and/or a VEGF ligand. In a preferred embodiment, the cancer is breast cancer.

The VEGF receptor antagonists of the present invention are suitable for use in treating any disease or disorder that would benefit from a disruption in the VEGF signaling pathway. In other words, the VEGF receptor antagonists can be used to treat a disease or disorder that is associated with undesirable vascularization. In addition to treating certain kinds of cancers, slowing cell proliferation and decreasing angiogenesis, the VEGF receptor antagonists of the present invention can be used to treat ischemia-related retinal disorders and other non-neoplastic conditions.

For example, the VEGF receptor antagonists of the present invention are useful in the treatment of various neoplastic diseases and disorders. Neoplasms and related conditions that are amenable to treatment include carcinomas of the breast, lung, esophagus, gastric anatomy, colon, rectum, liver, ovary, cervix, endometrium, thecomas, arrhenoblastomas, endometrial hyperplasia, endometriosis, fibrosarcomas, choriocarcinoma, head and neck cancer, nasopharyngeal carcinoma, laryngeal carcinoma, hepatoblastoma, Karposi's sarcoma, melanoma, skin carcinomas, hemangioma, cavernous hemangioma, hemangioblastoma, pancreas carcinoma, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, thyroid carcinomas, Wilm's tumor, renal cell carcinoma, prostate carcinoma, abnormal vascular proliferation associated with phakomatoses, edema (such as associated with brain tumors), and Meigs' syndrome.

Non-neoplastic conditions that are amenable to treatment include rheumatoid arthritis, psoriasis, atherosclerosis, diabetic and other retinopathies, retrolental fibroplasia, neovascular glaucoma, age-related macular degeneration, thyroid hyperplasias (including grave's disease), corneal and other tissue transplantation, chronic inflammation, lung inflammation, nephrotic syndrome, preclampasia, ascites, pericardial effusion (such as associated with pericarditis) and pleural effusion.

The therapeutic methods described herein involve administering to a subject in need of treatment a therapeutically effective amount of a fusion protein, VEGF receptor antagonist, polynucleotide encoding a VEGF receptor antagonist or a polynucleotide encoding a fusion protein. "Therapeutically effective" is employed here to denote the amount of fusion protein, polynucleotide or VEGF receptor antagonist that is of sufficient quantity to inhibit or decrease angiogenesis and/or cancer growth (e.g., induce apoptosis). Some methods contemplate combination therapy with known cancer medicaments or therapies, for example, chemotherapy or radiation. The patient may be a human or non-human animal.

Administration during in vivo treatment may be by any number of routes, including parenteral and oral, but preferably parenteral. Intracapsular, intravenous, intrathecal, and intraperitoneal routes of administration may be employed, generally intravenous is preferred. The skilled artisan will recognize that the route of administration will vary depending on the disorder to be treated.

Determining a therapeutically effective amount of the compositions of the present invention largely depend on particular patient characteristics, route of administration, and the nature of the disorder being treated. General guidance can be found, for example, in the publications of the International Conference on Harmonisation and in REMINGTON'S PHARMACEUTICAL SCIENCES, chapters 27 and 28, pp. 484-528 (Mack Publishing Company 1990).

Determining a therapeutically effective amount specifically will depend on such factors as toxicity and efficacy of the medicament. Toxicity may be determined using methods well known in the art and found in the foregoing references. Efficacy may be determined utilizing the same guidance in conjunction with the methods described below in the Examples. A pharmaceutically effective amount, therefore, is an amount that is deemed by the clinician to be toxicologically tolerable, yet efficacious. Efficacy, for example, can be measured by the decrease in mass of the targeted tissue. Suitable dosages can be from about 1-10 mg/kg KDR-Ig4-7.

The invention is further described by reference to the following examples, which are provided for illustration only. The invention is not limited to the examples but rather includes all variations that are evident from the teachings provided herein.

EXAMPLES

Example 1

Production and Purification KDR Receptor Antagonists

Three recombinant proteins (KDR (Ig4), KDR (Ig5-7) and KDR (Ig4-7)) were produced and purified. Recombinant proteins of the present invention can be produced from *E. coli.* according to published protocols (Cataldo et al., *Int. J. Oncol.* 17:1179-85 (2000)) with modifications.

Briefly, BL21 (DE3) cells (Novagen, Madison, Wis.) were transformed with plasmids encoding recombinant proteins using a calcium chloride method. The transformants were spread on an ampicillin plate, and grown overnight at 37° C. The LB seed culture was inoculated and grown overnight. The following day a LB growth culture was generated by inoculation of 5% of the seed culture and grown for ~2.5 hours at 37° C. with agitation. IPTG (Fisher Scientific) was added to the culture (1 mM final concentration) to induce expression of recombinant proteins and incubated for an additional 4 hours. Bacteria was pelleted and resuspended in a solution containing 0.2M $NaPO_4$ pH8, 10 mM EDTA, and 0.5% Triton X-100. The resuspended bacteria was lysed with a 550 Sonic Dismembrator (Fisher Scientific). The products, which were in the form of inclusion bodies, were pelleted and resuspended in 0.2M $NaPO_4$ pH7, 1% v/v beta mercaptoethanol, and 8M Urea for refolding. The refolding process consisted of dialyzing the protein against decreasing amounts of urea and beta-mercaptoethanol in the presence of 50 mM $NH_4HCO_3$, pH 8.0 for three consecutive days. The sample was then purified by a Q-Sepharose anionic exchange column (Pharmacia, Piscataway, N.J.) using a FPLC system (Pharmacia, Piscataway, N.J.).

Example 2

KDR (Ig4-7) Inhibited MAPK Phosphorylation in T-47D Human Breast Cancer Cells T-47D cells were cultured overnight in serum free media at 80% confluency and were treated for 60 minutes with G129R (10 µg/ml, ~0.5 µM); hPRL (100 ng/ml, ~5.0 nM), and KDR (Ig4-7) (25 µg/ml, ~0.5 µM) as compared to untreated cells (basal). Membranes were stripped and re-probed with anti-MAPK antibody to ensure equal loading. Results indicate that MAPK phosphorylation decreased in the presence of KDR (Ig4-7) compared to control samples. Thus, KDR (Ig4-7) blocks the ability of a full length KDR monomer to form a functional homodimer and effect VEGF signaling (FIG. 5).

Example 3

KDR (Ig4-7) and KDR (Ig5-7) Decreased Cell Proliferation in a Breast Cancer Cell Line The cell proliferation assay was performed according to Beck et al. (2003) (supra). MDA-MB 231 or T-47D cells (which are KDR positive cell lines) were grown in medium free of phenol-red. Fully confluent MDA-MB 231 and T-47D cell cultures were trypsinized and resuspended in a medium containing 5% fetal bovine serum (FBS). Cells were then seeded into 96-well culture plates at a density of 15,000 MDA-MB 231 cells/well or 15,000T-47D cells/well. After incubating the cells for 24 hours, various concentrations of tester proteins were added to the wells. Cells were further incubated for 48-72 hours at 37° C. in a humidified 5% $CO_2$ incubator. The viability of the cells was determined using the MTS-PMS (CellTiter 96 Aqueous Kit; Promega Corp., Madison, Wis.) colorimetric assay according to the manufacturer's protocol. Absorbance at 490 nm was determined using a microplate reader (BioRad).

Results indicated that KDR (Ig4-7) and KDR (Ig5-7) inhibited cell proliferation in a dose dependent manner (FIG. 2 and FIG. 3).

Example 4

Inhibition of Growth in Primary Xenografts

Human breast cancer cell lines T-47D and MDA-MB-435 are purchased from American Type Culture Collection (Rockville, Md.) and are cultured according to the vendor's instructions. Eight to ten-week old female Nuj/nude mice (The Jackson Lab, Bar Harbor, Me.) are used. The animals are maintained in a sterile environment in compliance with NIH guidelines.

Cells are grown in RPMI-1640 or DMEM medium, containing 10% FBS. The cells are maintained in a humidified atmosphere containing 5% $CO_2$ at 37C according to ATCC recommendation to 95-100% confluence. Adherent cells are detached using trypsin (0.25% 1 mM EDTA), counted, resuspended in Matrigel at a concentration of $1\times10^7$ cells/200 µl Matrigel, and injected into the mammary gland fat pad of Nuj/nude mice. The mice are implanted subcutaneously with slow-releasing E2 (17-β estradiol) pellets (0.72 mg/60 day, Innovative Research of America, Inc.) to enchance tumor growth (for T-47D group only). Three days after tumor cell innoculation, the mice are randomized into control and experimental groups and treated daily at 100 µg/mouse/day for at least 10 weeks.

Tumor size is monitored once a week and tumor volume is determined by measuring the length and width of the tumor mass. Tumor volume is calculated by the following formula: $(L\times W^2)/2$. Tumors are dissected at the end of the experiments and weighed. Treated and control mice are compared as a function of time, using repeated measures analysis of variance (ANOVA). The tumor growth curves are compared among the groups.

Results indicate that tumor cell growth is slowed in the breast cancer xenograft animal models. Thus, KDR (Ig4-7) is suitable for use in slowing the progression of breast cancer.

Example 5

KDR Antagonist Fusion Proteins

KDR (Ig4-7) or KDR (Ig4) are fused to G129R, a proven prolactin receptor antagonist comprising a single binding site to the prolactin receptor. This fusion protein is a single molecule with two binding sites for two different receptors, both of which are located on a breast cancer cell (i.e., KDR and the prolactin receptor). The G129R-KDR (Ig4-7) fusion protein and G129R-KDR (Ig4) form heterodimers with a full length KDR when applied to cancer cells and therefore, antagonize both the prolactin and VEGF signaling pathways. Microgram/milliliter concentrations are needed to achieve maximum inhibition.

Example 6

KDR Antagonists Specifically Bind HUVEC

KDR (Ig4-7) protein (49 kDa) was produced in *E. coli* and purified using a FLCE system along with two control proteins, KDR (Ig5-7) (38 kDa) and KDR (Ig4) (11 kDa). $^{125}$I-labeled KDR (Ig4-7) specifically bound to human umbilical vein endothelial cells (HUVEC), a cell line that expresses high levels of KDR with an EC50 value at approximately 10 μg/ml (FIG. 6). Total binding of KDR (Ig4-7) was also compared between HUVEC and two human breast cancer cell lines that were reported to have KDR expression (T47-D and MCF-7 cell lines) (FIG. 7). Specific binding of KDR (Ig4-7) was approximately 88%.

What is claimed is:

1. A VEGF receptor antagonist consisting of KDR (Ig5-7).
2. A soluble VEGF receptor antagonist that consists essentially of SEQ ID NO:2.
3. A soluble VEGF receptor antagonist that consists essentially of SEQ ID NO:4.
4. The soluble VEGF receptor antagonist of claim 2, consisting of SEQ ID NO:2.
5. The soluble VEGF receptor antagonist of claim 3, consisting of SEQ ID NO:4.

* * * * *

UNITED STATES PATENT AND TRADEMARK OFFICE
CERTIFICATE OF CORRECTION

PATENT NO. : 7,582,726 B2
APPLICATION NO. : 10/985013
DATED : September 1, 2009
INVENTOR(S) : Chen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 132 days.

Signed and Sealed this

Fourteenth Day of September, 2010

David J. Kappos
*Director of the United States Patent and Trademark Office*

SEQUENCE LISTING

<160> NUMBER OF SEQ ID NOS: 4

<210> SEQ ID NO 1
<211> LENGTH: 1281
<212> TYPE: DNA
<213> ORGANISM: Homo sapiens

<400> SEQUENCE: 1

```
atggcattca tcactgtgaa acatcgaaaa cagcaggtgc ttgaaaccgt agctggcaag      60
cggtcttacc ggctctctat gaaagtgaag gcatttccct cgccggaagt tgtatggtta     120
aaagatgggt tacctgcgac tgagaaatct gctcgctatt tgactcgtgg ctactcgtta     180
attatcaagg acgtaactga agaggatgca gggaattata caatcttgct gagcataaaa     240
cagtcaaatg tgtttaaaaa cctcactgcc actctaattg tcaatgtgaa accccagatt     300
tacgaaaagg ccgtgtcatc gtttccagac ccggctctct acccactggg cagcagacaa     360
atcctgactt gtaccgcata tggtatccct caacctacaa tcaagtggtt ctggcacccc     420
tgtaaccata atcattccga agcaaggtgt gactttttgtt ccaataatga agagtccttt     480
atcctggatg ctgacagcaa catgggaaac agaattgaga gcatcactca gcgcatggca     540
ataatagaag gaaagaataa gatggctagc accttggttg tggctgactc tagaatttct     600
ggaatctaca tttgcatagc ttccaataaa gttgggactg tgggaagaaa cataagcttt     660
tatatcacag atgtgccaaa tgggtttcat gttaacttgg aaaaaatgcc gacggaagga     720
gaggacctga aactgtcttg cacagttaac aagttcttat acagagacgt tacttggatt     780
ttactgcgga cagttaataa cagaacaatg cactacagta ttagcaagca aaaaatggcc     840
atcactaagg agcactccat cactcttaat cttaccatca tgaatgtttc cctgcaagat     900
tcaggcacct atgcctgcag agccaggaat gtatacacag gggaagaaat cctccagaag     960
aaagaaatta caatcagaga tcaggaagca ccatacctcc tgcgaaacct cagtgatcac    1020
acagtggcca tcagcagttc caccacttta gactgtcatg ctaatggtgt ccccgagcct    1080
cagatcactt ggtttaaaaa caaccacaaa atacaacaag agcctggaat tatttttagga    1140 ccaggaagca gcacgctgtt tattgaaaga gtcacagaag aggatgaagg tgtctatcac    1200
tgcaaagcca ccaaccagaa gggctctgtg gaaagttcag catacctcac tgttcaagga    1260
```
acctcggaca agtctaatta g    1281

<210> SEQ ID NO 2
<211> LENGTH: 434
<212> TYPE: PRT
<213> ORGANISM: Homo sapiens

<400> SEQUENCE: 2

His Met Phe Val Ala Phe Gly Ser Gly Met Glu Ser Leu Val Glu Ala
 1               5                  10                  15

Thr Val Gly Glu Arg Val Arg Ile Pro Ala Lys Tyr Leu Gly Tyr Pro
             20                  25                  30

Pro Pro Glu Ile Lys Trp Tyr Lys Asn Gly Ile Pro Leu Glu Ser Asn
         35                  40                  45

His Thr Ile Lys Ala Gly His Val Leu Thr Ile Met Glu Val Ser Glu
     50                  55                  60

Arg Asp Thr Gly Asn Tyr Thr Val Ile Leu Thr Asn Pro Ile Ser Lys
 65                  70                  75                  80

Glu Lys Gln Ser His Val Val Ser Leu Val Val Tyr Val Pro Pro Gln
                 85                  90                  95

Ile Gly Glu Lys Ser Leu Ile Ser Pro Val Asp Ser Tyr Gln Tyr Gly
            100                 105                 110

Thr Thr Gln Thr Leu Thr Cys Thr Val Tyr Ala Ile Pro Pro Pro His
        115                 120                 125

His Ile His Trp Tyr Trp Gln Leu Glu Glu Cys Ala Asn Glu Pro
    130                 135                 140

Ser Gln Ala Val Ser Val Thr Asn Pro Tyr Pro Cys Glu Glu Trp Arg
145                 150                 155                 160

Ser Val Glu Asp Phe Gln Gly Gly Asn Lys Ile Glu Val Asn Lys Asn
                165                 170                 175

Gln Phe Ala Leu Ile Glu Gly Lys Asn Lys Thr Val Ser Thr Leu Val
            180                 185                 190

Ile Gln Ala Ala Asn Val Ser Ala Leu Tyr Lys Cys Glu Ala Val Asn
        195                 200                 205

Lys Val Gly Arg Gly Glu Arg Val Ile Ser Phe His Val Thr Arg Gly
    210                 215                 220

Pro Glu Ile Thr Leu Gln Pro Asp Met Gln Pro Thr Glu Gln Glu Ser
225                 230                 235                 240

Val Ser Leu Trp Cys Thr Ala Asp Arg Ser Thr Phe Glu Asn Leu Thr
                245                 250                 255

Trp Tyr Lys Leu Gly Pro Gln Pro Leu Pro Ile His Val Gly Glu Leu
            260                 265                 270

Pro Thr Pro Val Cys Lys Asn Leu Asp Thr Leu Trp Lys Leu Asn Ala
        275                 280                 285

Thr Met Phe Ser Asn Ser Thr Asn Asp Ile Leu Ile Met Glu Leu Lys
    290                 295                 300

Asn Ala Ser Leu Gln Asp Gln Gly Asp Tyr Val Cys Leu Ala Gln Asp
305                 310                 315                 320

Arg Lys Thr Lys Lys Arg His Cys Val Val Arg Gln Leu Thr Val Leu
                325                 330                 335

Glu Arg Val Ala Pro Thr Ile Thr Gly Asn Leu Glu Asn Gln Thr Thr
            340                 345                 350

Ser Ile Gly Glu Ser Ile Glu Val Ser Cys Thr Ala Ser Gly Asn Pro
        355                 360                 365

```
Pro Pro Gln Ile Met Trp Phe Lys Asp Asn Glu Thr Leu Val Glu Asp
    370                 375                 380

Ser Gly Ile Val Leu Lys Asp Gly Asn Arg Asn Leu Thr Ile Arg Arg
385                 390                 395                 400

Val Arg Lys Glu Asp Glu Gly Leu Tyr Thr Cys Gln Ala Cys Ser Val
                405                 410                 415

Leu Gly Cys Ala Lys Val Glu Ala Phe Phe Ile Ile Gly Gly Ala Gln
            420                 425                 430

Glu Lys

<210> SEQ ID NO 3
<211> LENGTH: 1146
<212> TYPE: DNA
<213> ORGANISM: Homo sapiens

<400> SEQUENCE: 3
atgcatgtac tgacgattat ggaagtgagt gaaagagaca caggaaatta cactgtcatc      60
cttaccaatc ccatttcaaa ggagaagcag agccatgtgg tctctctggt tgtgtatgtc     120
ccaccccaga ttggtgagaa atctctaatc tctcctgtgg attcctacca gtacggcacc     180
actcaaacgc tgcatgtgta ggtctatgcc attcctcccc cgcatcacat ccactggtat     240
tggcagttgg aggaagagtg cgccaacgag cccagccaag ctgtctcagt gacaaaccca     300
taccctggtg aagaatggag aagtgtggag gacttccagg gaggaaataa aattgaagtt     360
aataaaaatc aatttgctct aattgaagga aaaacaaaaa ctgtaagtac ccttgttatc     420
caagcggcaa atgtgtcagc tttgtacaaa tgtgaagcgg tcaacaaagt cgggagagga     480 gagggtgatctccttccacgtgaccagggtcctgaaattactttgcaacctgacatg     540 cagcccactg agcaggagag cgtgtctttg tggtgcactg cagacagatc tacgtttgag     600
aacctcacat ggtacaagct ggcccacag cctctgccaa tccatgtggg agagttgccc     660
acacctgttt gcaagaactt ggatactctt tggaaattga atgccaccat gttctctaat     720
agcacaaatg acatttttgat catggagctt aagaatgcat ccttgcagga ccaaggagac     780
tatgtctgcc ttgctcaaga caggaagacc aagaaaagac attgcgtggt caggcagctc     840
acagtcctag agcgtgtggc acccacgatc acaggaaacc tggagaatca gacgacaagt     900
attggggaaa gcatcgaagt ctcatgcacg gcatctggga atcccctcc acagatcatg     960 tgggttaaag ataatgagac ccttgtagaa gactcaggca ttgtattgaa ggatgggaac     1020
cggaacctca ctatccgcag agtgaggaag gaggacgaag gcctctacac ctgccaggca     1080
tgcagtgttc ttggctgtgc aaaagtggag gcattttctca taatagaagg tgcccaggaa     1140
aagtaa                                                                1146

<210> SEQ ID NO 4
<211> LENGTH: 381
<212> TYPE: PRT
<213> ORGANISM: Homo sapiens

<400> SEQUENCE: 4

Met His Val Leu Thr Ile Met Glu Val Ser Glu Arg Asp Thr Gly Asn
1               5                   10                  15

Tyr Thr Val Ile Leu Thr Asn Pro Ile Ser Lys Glu Lys Gln Ser His
            20                  25                  30

Val Val Ser Leu Val Val Tyr Val Pro Pro Gln Ile Gly Glu Lys Ser
        35                  40                  45
```

```
Leu Ile Ser Pro Val Asp Ser Tyr Gln Tyr Gly Thr Thr Gln Thr Leu
        50                  55                  60

Thr Cys Thr Val Tyr Ala Ile Pro Pro His His Ile His Trp Tyr
 65              70              75              80

Trp Gln Leu Glu Glu Glu Cys Ala Asn Glu Pro Ser Gln Ala Val Ser
                85                  90                  95

Val Thr Asn Pro Tyr Pro Cys Glu Glu Trp Arg Ser Val Glu Asp Phe
            100                 105                 110

Gln Gly Gly Asn Lys Ile Glu Val Asn Lys Asn Gln Phe Ala Leu Ile
            115                 120                 125

Glu Gly Lys Asn Lys Thr Val Ser Thr Leu Val Ile Gln Ala Ala Asn
            130                 135                 140

Val Ser Ala Leu Tyr Lys Cys Glu Ala Val Asn Lys Val Gly Arg Gly
145                 150                 155                 160

Glu Arg Val Ile Ser Phe His Val Thr Arg Gly Pro Glu Ile Thr Leu
                165                 170                 175

Gln Pro Asp Met Gln Pro Thr Glu Gln Glu Ser Val Ser Leu Trp Cys
            180                 185                 190

Thr Ala Asp Arg Ser Thr Phe Glu Asn Leu Thr Trp Tyr Lys Leu Gly
        195                 200                 205

Pro Gln Pro Leu Pro Ile His Val Gly Glu Leu Pro Thr Pro Val Cys
        210                 215                 220

Lys Asn Leu Asp Thr Leu Trp Lys Leu Asn Ala Thr Met Phe Ser Asn
225                 230                 235                 240

Ser Thr Asn Asp Ile Leu Ile Met Glu Leu Lys Asn Ala Ser Leu Gln
            245                 250                 255

Asp Gln Gly Asp Tyr Val Cys Leu Ala Gln Asp Arg Lys Thr Lys Lys
            260                 265                 270

Arg His Cys Val Val Arg Gln Leu Thr Val Leu Glu Arg Val Ala Pro
        275                 280                 285

Thr Ile Thr Gly Asn Leu Glu Asn Gln Thr Thr Ser Ile Gly Glu Ser
        290                 295                 300

Ile Glu Val Ser Cys Thr Ala Ser Gly Asn Pro Pro Pro Gln Ile Met
305                 310                 315                 320

Trp Phe Lys Asp Asn Glu Thr Leu Val Glu Asp Ser Gly Ile Val Leu
                325                 330                 335

Lys Asp Gly Asn Arg Asn Leu Thr Ile Arg Arg Val Arg Lys Glu Asp
            340                 345                 350

Glu Gly Leu Tyr Thr Cys Gln Ala Cys Ser Val Leu Gly Cys Ala Lys
        355                 360                 365

Val Glu Ala Phe Phe Ile Ile Glu Gly Ala Gln Glu Lys
        370                 375                 380
```